US008606346B2

(12) United States Patent
Parel et al.

(10) Patent No.: US 8,606,346 B2
(45) Date of Patent: *Dec. 10, 2013

(54) INTRAOPERATIVE MONITORING OF TEMPERATURE-INDUCED TISSUE CHANGES WITH A HIGH-RESOLUTION DIGITAL X-RAY SYSTEM DURING THERMOTHERAPY

(75) Inventors: Jean-Marie Parel, Miami Shores, FL (US); Fabrice Manns, Coral Gables, FL (US); David S. Robinson, Kansas City, MO (US); Peter Milne, Miami, FL (US); David B. Denham, Miami, FL (US); Xochitl Gonzalez-Cirre, Madrid (ES)

(73) Assignee: University of Miami, Miami, FL (US)

( * ) Notice: Subject to any disclaimer, the term of this patent is extended or adjusted under 35 U.S.C. 154(b) by 2 days.

This patent is subject to a terminal disclaimer.

(21) Appl. No.: 13/289,709

(22) Filed: Nov. 4, 2011

(65) Prior Publication Data
US 2012/0101375 A1  Apr. 26, 2012

Related U.S. Application Data

(63) Continuation of application No. 12/081,278, filed on Apr. 14, 2008, now Pat. No. 8,099,147, which is a continuation of application No. 10/727,137, filed on Dec. 3, 2003, now abandoned, which is a continuation of application No. 09/556,958, filed on Apr. 21, 2000, now Pat. No. 6,684,097.

(60) Provisional application No. 60/130,497, filed on Apr. 22, 1999.

(51) Int. Cl.
*A61B 5/00* (2006.01)

(52) U.S. Cl.
USPC ........... 600/407; 600/411; 600/427; 600/437; 382/128; 382/130; 382/131

(58) Field of Classification Search
USPC .......................... 600/407, 427, 437; 382/128
See application file for complete search history.

(56) References Cited

U.S. PATENT DOCUMENTS

| 4,638,436 A | 1/1987 | Badger et al. |
| 4,922,916 A | 5/1990 | Ermert et al. |

(Continued)

FOREIGN PATENT DOCUMENTS

| JP | 1218466 | 8/1989 |
| WO | 97/20193 | 6/1997 |

OTHER PUBLICATIONS

Akimov et al., "Histological Changes in Human Breast Cancer After Interstitial Irradiation with a Pulsed ND-YAG Laser," Lasers in Medical Science, vol. 12, 1997, pp. 165-169.

(Continued)

*Primary Examiner* — Baisakhi Roy
(74) *Attorney, Agent, or Firm* — Alston & Bird LLP

(57) ABSTRACT

A method of thermally inducing and monitoring changes to localized regions of tissue by illuminating a volume of tissue with a first beam of X-rays, detecting portions of the first beam that passed through the volume, generating a first image signal from the portions of the first beam detected, applying heat to at least a localized region of tissue within the volume after the illuminating and detecting, illuminating the volume with a second beam of X-rays, detecting portions of the second beam that passed through the volume during the illuminating with the second beam, generating a second image signal from the portions of the second beam detected, and generating a difference image signal based upon a comparison of the first and second image signals. The difference image signal provides information of changes in X-ray attenuation by localized regions of tissue within the volume due to the application of heat.

17 Claims, 31 Drawing Sheets

(56) References Cited

U.S. PATENT DOCUMENTS

| | | | |
|---|---|---|---|
| 5,078,142 A | | 1/1992 | Siczek et al. |
| 5,222,953 A | | 6/1993 | Dowlatshahi |
| 5,298,026 A | | 3/1994 | Chang |
| 5,348,551 A | | 9/1994 | Spears et al. |
| 5,365,562 A | | 11/1994 | Toker |
| 5,370,121 A | | 12/1994 | Reichenberger et al. |
| 5,388,581 A | | 2/1995 | Bauer et al. |
| 5,485,839 A | | 1/1996 | Aida et al. |
| 5,526,394 A | | 6/1996 | Siczek et al. |
| 5,531,738 A | | 7/1996 | Hessel et al. |
| 5,553,618 A | | 9/1996 | Suzuki et al. |
| 5,590,655 A | | 1/1997 | Hussman |
| 5,657,760 A | | 8/1997 | Ying et al. |
| 5,782,762 A | | 7/1998 | Vining |
| 5,807,395 A | | 9/1998 | Mulier et al. |
| 5,859,891 A | | 1/1999 | Hibbard |
| 5,917,881 A | | 6/1999 | Jeffery |
| 5,944,663 A | * | 8/1999 | Kuth et al. ............... 600/411 |
| 6,067,371 A | | 5/2000 | Gouge et al. |
| 6,157,854 A | | 12/2000 | Haber et al. |
| 6,163,726 A | | 12/2000 | Wolf |
| 6,249,594 B1 | | 6/2001 | Hibbard |
| 6,375,634 B1 | * | 4/2002 | Carroll ..................... 604/19 |
| 6,488,697 B1 | * | 12/2002 | Ariura et al. ................ 607/89 |
| 6,575,969 B1 | | 6/2003 | Rittman, III et al. |
| 6,684,097 B1 | * | 1/2004 | Parel et al. ................ 600/427 |
| 6,914,959 B2 | | 7/2005 | Bailey et al. |
| 7,476,235 B2 | * | 1/2009 | Diederich et al. .......... 606/192 |
| 7,871,406 B2 | * | 1/2011 | Nields et al. ............... 606/27 |
| 8,099,147 B2 | * | 1/2012 | Parel et al. ................ 600/407 |
| 8,155,416 B2 | * | 4/2012 | Nields et al. .............. 382/131 |
| 2001/0039417 A1 | | 11/2001 | Harano et al. |
| 2002/0114499 A1 | | 8/2002 | Breitenstein et al. |
| 2003/0007601 A1 | | 1/2003 | Jaffray et al. |
| 2004/0015163 A1 | | 1/2004 | Buysse et al. |
| 2005/0059623 A1 | | 3/2005 | Moonen |

OTHER PUBLICATIONS

Akimov et al., "ND:YAG Interstitial Laser Thermotherapy in the Treatment of Breast Cancer," Lasers in Surgery and Medicine, vol. 22, 1998, pp. 257-267.
Amin et al., "Hepatic metastasis: interstitial laser photocoagulation with real-time US monitoring and dynamic CT evaluation of treatment," Radiology, vol. 187, 1993, pp. 339-347.
Ascher et al., "MR-Guided Laser Assisted Thermotheraphy of Cerebral BFMN Tumors," SPIE Optical Engineering Press, Bellingham, Washington, 1995, pp. 377-381.
Bentzen et al., "Isotherm mapping in hyperthermia using substraction X-ray computed tomography," Radiotherapy and Oncology, vol. 2, 1984, pp. 255-260.
Bettag et al., "Neurological and Functional Changes After Laser-Induced Interstitial Thermotherapy (LITT) of Brain Tumors," SPIE Optical Engineering Press, Bellingham, Washington, 1995, pp. 382-392.
Beuthan et al., "Investigations of MRI Sequences (SPIN-ECHO; Turbo-Flash) for Laser-Induced Thermo Therapy Monitoring," SPIE Optical Engineering Press, Bellingham, Washington, 1995, pp. 279-287.
Bown, "Phototherapy of tumours," World Journal of Surgery, vol. 7, 1983, pp. 700-709.
Bydder et al., "The temperature dependence of computed tomography attenuation values," Journal of Computer Assisted Tomography, vol. 3, 1979, pp. 506-510.
Cholewa et al., "Magnetic resonance imaging: controlled interstitial laser therapy in children with vascular malformations," Lasers in Surgery and Medicine, vol. 23, 1998, pp. 250-257.
"Clinical Applications," SPIE Optical Engineering Press, Bellingham, Washington, Co-editor S.G. Brown, 1995, pp. 375-376.
De Jode et al., "MRI guidance of infra-red laser liver tumour ablations, utilizing an open MRI configuration system: technique and early progress," Journal of Hepatology, vol. 31, 1999, pp. 347-353.

Desinger et al., "Radio-Frequency Current Application for Interstitial Thermotherapy (RF-ITT), an Alternative or Completion to LITT?—Future Prospects—," SPIE Optical Engineering Press, Bellingham, Washington, 1995, pp. 530-541.
Dowlatshahi et al., "Stereotaxic Interstitial Laser Therapy of Early-Stage Breast Cancer," The Breast Journal, vol. 2, No. 5, 1996, pp. 304-311.
Eyrich et al., "Temperature mapping of magnetic resonance-guided laser interstitial thermal therapy (LITT) in lymphangiomas of the head and neck," Lasers in Surgery Medicine, vol. 26, 2000, pp. 467-476.
Fallone et al., "Noninvasive Thermotherapy with a Clinical X-Ray CT Scanner," Med. Phys., vol. 9, No. 5, Sep. 1982, pp. 715-721.
Feyh et al., "MRI-guided laser interstitial thermal therapy (LITT) of head and neck tumors: Progress with a new method," Journal of Clinical Laser Medicine and Surgery, vol. 14, 1996, pp. 361-366.
Germer et al., "Laser-Induced Thermotherapy (LITT) in the Treatment of Colorectal Liver Metastases—A Clinical Pilot Study," SPIE Optical Engineering Press, Bellingham, Washington, 1995, pp. 393-402.
Gewiese et al., "Magnetic resonance imaging-controlled laser-induced thermotherapy," Investigative Radiology, vol. 29, 1994, pp. 345-351.
Guiot et al., "Perfusion and thermal field during hyperthermia. Experimental measurements and modeling in recurrent breast cancer," Physics in Medicine and Biology, vol. 43, 1998, pp. 2831-2843.
Handke et al., "Laser-Induced Interstitial Thermotherapy (LITT) of Benign Prostatic Hyperplasia (BPH)—Basic Investigations and First Clinical Results," SPIE Optical Engineering Press, Bellingham, Washington, 1995, vol. 403-415.
Henkel et al., "Transurethral and Transperineal Interstitial Laser Therapy of BPH," SPIE Optical Engineering Press, Bellingham, Washington, 1995, pp. 416-425.
Ivarsson et al., "Feedback interstitial diode laser (805 nm) thermotherapy system: ex vivo evaluation and mathematical modeling with one and four-fibers," Lasers in Surgery and Medicine, vol. 22, 1998, pp. 86-96.
Jenne et al., "CT On-Line Monitoring of HIFU Therapy," 1997 IEEE Ultrasonics Symposium, vol. 2, Oct. 1997, pp. 1377-1380.
Jolesz, "Monitoring and Control of Interstitial Laser Thermotherapy," Co-editor F.A. Jolesz, SPIE Optical Engineering Press, Bellingham, Washington, 1995, p. 265.
Jolesz et al., "MRI-Guided Laser-Induced Interstitial Thermotherapy: Basic Principles," SPIE Optical Engineering Press, Bellingham, Washington, 1995, pp. 294-324.
Kahn et al., "MRI-guided laser-induced interstitial thermotherapy of cerebral neoplasms," Journal of Computer Assisted Tomography, vol. 18, 1994, pp. 519-532.
Kahn et al., "MRI-Guidance of Laser-Induced Interstitial Thermotherapy of Brain Tumors—Three Year Experience," SPIE Optical Engineering Press, Bellingham, Washington, 1995, pp. 325-339.
Kettenbach et al., "Monitoring and visualization techniques for MR-guided laser ablations in an open MR system," Journal of Magnetic Resonance Imaging, vol. 8, 1998, pp. 933-943.
Mann et al., "In Situ Temperature Measurements with Thermocouple Probes During Laser Interstitial Thermotherapy (LITT): Quantification and Correction of a Thermotherapy (LITT): Quantification and Correction of a Measurement Artifact" Lasers in Surgery and Medicine, vol. 23, No. 2, May 1998, pp. 94-103.
Masters et al., "Interstitial laser hyperthermia," Seminars in Surgical Oncology, vol. 8, 1992, pp. 242-249.
Milne et al., "Development of stereotactically-guided laser interstitial thermotherapy (LITT) of breast cancer: in-situ measurement and analysis of the temperature field in ex vivo and in vivo adipose tissue," Lasers in Surgery and Medicine, vol. 26, 2000, pp. 67-75.
Muller et al., "Computertomographisch gesteuerte Positionierung von Kathetern zur Temperaturmessung bei der Hyperthermie maligner Tumoren," Strahlentherapie and Onkologie, vol. 164, 1988, pp. 593-601.
Muller et al., "Laser-Induced Interstitial Thermotherapy (LITT)," Editors Gerhard Muller and Andre Roggan, SPIE Optical Engineering Press, Bellingham, Washington, 1995, pp. 3-5.

(56) References Cited

OTHER PUBLICATIONS

Mueller-Lisse et al., "Coagulative inerstitial laser-induced thermotherapy of benign prostatic hyperplasia: online imaging with a T2-weighted fast spin echo MR sequence. Experience in six patients," Radiology, vol. 210, 1999, pp. 373-379.

Mueller-Lisse et al., "Magnetic Resonance Imaging in Laser Induced Thermo Therapy of the Prostate," SPIE Optical Engineering Press, Bellingham, Washington, 1995, pp. 340-343.

Mumtaz et al., "The Potential of Interstitial Laser Photocoagulation in the Treatment of Breast Cancer," SPIE Optical Engineering Press, Bellingham, Washington, 1995, pp. 426-433.

Muschter et al., "Clinical Results of LITT in the Treatment of Benign Prostatic Hyperplasia," SPIE Optical Engineering Press, Bellingham, Washington, 1995, pp. 434-442.

Muschter et al., "Laser-Tissue Interaction Changes with the 805 nm Diode Laser Using Indocyanine Green in the Canine Prostate," SPIE Optical Engineering Press, Bellingham, Washington, 1995, pp. 510-515.

Nolsoe et al., "Interstitial hyperthermia of colorectal liver metastases with a US-guided Nd-YAG laser with a diffuser tip: a pilot clinical study," Radiology, vol. 187, 1993, pp. 333-337.

Peters et al., "Magnetic resonance thermometry for predicting thermal damage: An application of interstitial laser coagulation in an in vivo canine prostate model," Magnetic Resonance in Medicine, vol. 44, 2000, pp. 873-883.

Philipp et al., "Treatment of Congenital Vascular Disorders (CVD) with Laser Induced Thermotherapy (LITT)," SPIE Optical Engineering Press, Bellingham, Washington, 1995, pp. 443-457.

Prapavat et al., "Investigation on the Feasibility of NIR-Transillumination Techniques for Detection of Interstitially Coagulated Tissue," SPIE Optical Engineering Press, Bellingham, Washington, 1995, pp. 516-529.

Prapavat et al., "In vitro studies and computer simulations to assess the use of a diode laser (850 nm) for laser-induced thermotherapy (LITT)," Lasers in Surgery and Medicine, vol. 18, 1996, pp. 22-23.

Reidenbach, "Future Prospects in Interstitial Thermotherapy," SPIE Optical Engineering Press, Bellingham, Washington, 1995, pp. 507-509.

Roberts et al., "Guidance and Control of Interstitial Laser Photocoagulation in Liver Tumors," SPIE Optical Engineering Press, Bellingham, Washington, 1995, pp. 344-353.

Robinson et al., "Stereotactic uses beyond core biopsy: model development for minimally invasive treatment of breast cancer through interstitial laser hyperthermia," American Surgeon, vol. 62, 1996, pp. 117-118.

Robinson et al., "Interstitial Laser Hyperthermia Model Development for Minimally Invasive Therapy of Breast Carcinoma," J Am Coll Surg, vol. 186, No. 3, Mar. 1998, pp. 284-292.

Rohde et al., "Monitoring of Interstitial Laser Induced Thermotherapy (LITT) with Color-Coded Duplexsonography (CCDS)," SPIE Optical Engineering Press, Bellingham, Washington, 1995, pp. 267-278.

Salas et al., "Development of a tissue phantom for experimental studies on laser interstitial thermotherapy of breast cancer," 0 SPIE Conference Proceedings, vol. 3907, Lasers in Surgery: Advanced Characterization, Therapeutics, and Systems X, 2000, pp. 603-631.

Schroder et al., "Percutaneous interstitial laser hyperthermia in clinical use," Annales Chirurgiae et Gynaecologiae, vol. 83, 1994, pp. 286-290.

Steger et al., "Interstitial laser hyperthermia: a new approach to local destruction of tumours," British Medical Journal, vol. 299, 1989, pp. 362-365.

Steger et al., "Ultrasound features of low-power laser hyperthermia," Clinical Radiology, vol. 46, 1992, pp. 88-93.

Sturesson et al., "A mathematical model for predicting the temperature distribution in laser-induced hyperthermia. Experimental evaluation and applications," Physics in Medicine and Biology, vol. 40, 1995, pp. 2037-2052.

Thomsen et al., "Identification of Lethal Thermal Injury at the Time of Photothermal Treatment," SPIE Optical Engineering Press, Bellingham, Washington, 1995, pp. 459-467.

Tranberg et al., "Interstitial Laser Thermotherapy Using Feedback Control and Monitoring with Electrical Impedance Tomography: Review of Studies In Vitro and In Vivo," SPIE Optical Engineering Press, Bellingham, Washington, 1995, pp. 354-365.

Tranberg et al., "Interstitial Laser Treatment: Preliminary Experience in Patients," SPIE Optical Engineering Press, Bellingham, Washington, 1995, pp. 468-476.

van Hillegersberg, "Ultrasonography of Laser-Induced Coagulation of Hepatic Metastases", SPIE Optical Engineering Press, Bellingham, Washington, 1995, pp. 288-293.

Vogl et al., "MR-Guided Laser-Induced Thermotherapy (LITT) of Liver Metastases," SPIE Optical Engineering Press, Bellingham, Washington, 1995, pp. 477-492.

Vogl et al., "MR-Guided Laser Induced Thermotherapy of Head and Neck Tumors," SPIE Optical Engineering Press, Bellingham, Washington, 1995, pp. 493-504.

Vogl et al., "Recurrent nasopharyngeal tumors: Preliminary clinical results with interventional MR imaging controlled laser-induced thermotherapy," Radiology, vol. 196, 1995, pp. 725-733.

Vogl et al., "Malignant liver tumors treated with MR imaging guided laser-induced thermotherapy: technique and prospective results," Radiology, vol. 196, 1995, pp. 257-265.

Wallwiener et al., "Laser Induced Interstitial Thermotheraphy LITT Versus High-Frequency Induced Thermotherapy HFTT," SPIE Optical Engineering Press, Bellingham, Washington, 1995, pp. 542-548.

Wallwiener et al., "Study About the On-Line Monitoring by Ultrasonography of the Spreading of Tissue Necrosis in Heterogenous Tissue Induced by Interstitial Thermotherapy," SPIE Optical Engineering Press, Bellingham, Washington, 1995, pp. 366-371.

Weber et al., "In Vivo Temperature Measurement During Transcatheter Endomyocardial ND-YAG Laser Irradiation in Dogs," Lasers in Medical Science, vol. 12, 1997, pp. 352-356.

Wust et al., "Rationale for using invasive thermotherapy for regional hyperthermia of pelvic tumors," International Journal of Radiation Oncology Biol. Phys., vol. 41, 1998, pp. 1129-1137.

Zamenhof et al., "Comments on 'Noninvasive Thermometry with a Clinical X-Ray CT Scanner'," Med. Phys., vol. 10, No. 3, May 1983, p. 374.

Zientara et al., "MRI-monitoring of laser ablation using optical flow," Journal of Magnetic Resonance Imaging, vol. 8, 1998, pp. 1306-1318.

International Preliminary Examination Report (IPER) in International Application No. PCT/US00/10814 completed Jun. 21, 2001.

Communications dated Aug. 30, 2004, Feb. 24, 2005, Sep. 1, 2005, Jul. 17, 2006, Jul. 27, 2006 and Jan. 11, 2007 in EP Application No. 00 926 246.0.

* cited by examiner

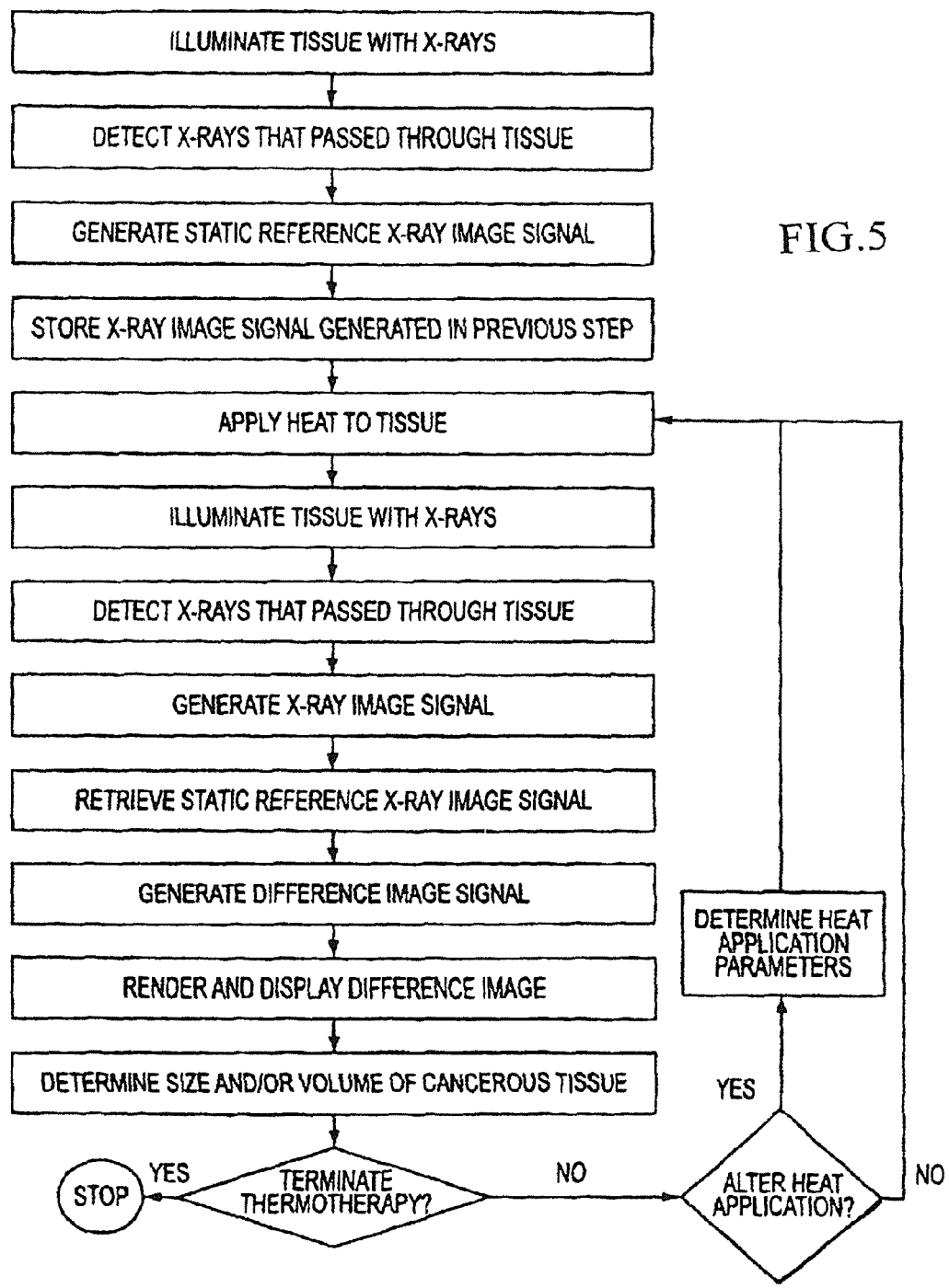

INTRAOPERATIVE MONITORING OF TEMPERATURE-INDUCED TISSUE CHANGES WITH A HIGH-RESOLUTION DIGITAL X-RAY SYSTEM DURING THERMOTHERAPY

RELATED APPLICATIONS

This application is a continuation of U.S. patent application Ser. No. 12/081,278 filed on Apr. 14, 2008, which in turn is a continuation of U.S. patent application Ser. No. 10/727,137 filed on Dec. 3, 2003 (now abandoned), which in turn is a continuation of U.S. patent application Ser. No. 09/556,958 filed on Apr. 21, 2000 (now U.S. Pat. No. 6,684,097 issued on Jan. 27, 2004), which claims the priority benefit of U.S. Provisional Application No. 60/130,497, filed on Apr. 22, 1999. The foregoing applications are incorporated herein by reference in their entirety.

The U.S. Government has a paid-up license in this invention and the right in limited circumstances to require the patent owner to license others on reasonable terms as provided for by the terms of Grant or Contract No.: USAMRDC/AIBS#2459, log #B4340289, 9/15/94 to Sep. 14, 1996, awarded by the Department of Defense

BACKGROUND OF THE INVENTION

1. Field of the Invention

This invention pertains to intraoperative monitoring methods and devices, and more particularly to intraoperative monitoring devices and methods for monitoring temperature-induced changes to tissue with high resolution digital X-ray imaging and inducing the changes to the tissue.

2. Discussion of Related Art

Various types of thermotherapy have been considered, and/or applied to the treatment of cancers. Laser interstitial thermotherapy (LITT) has received attention as a surgical procedure for the treatment of cancer tumors, and particularly with respect to liver, head, neck and breast cancer.

Laser interstitial thermotherapy is a surgical procedure for the treatment of cancer tumors in which near infra-red laser energy is delivered to the tumor site inside the body through a flexible fiber-optic probe. Some fiber optic probes in use terminate with a light diffusing tip. The infra-red laser radiation is absorbed by the tumor cells, which results in a temperature increase and subsequent cell death of the tumor cells. The temperature distribution around the light-diffusing tip, and thus the extent of cell-death, is a function of the laser parameters, treatment time, tumor size, and shape, fiber optic tip geometry, optical properties of the tumor, and blood perfusion rates in both compressed and uncompressed treatment sites.

The treatment parameters (e.g., wavelength, power, duration, tip geometry, and tip location and orientation) must be selected so as to minimize collateral damage to healthy tissue surrounding the tumor, yet still must ensure reliable total tumor destruction. Because of tissue inhomogeneities, and inter-patient variability of the physical and biological properties of tumors, intraoperative monitoring of the treatment effect is highly desirable. Currently, intraoperative monitoring of LITT is conducted with magnetic resonance imaging (MRI) or three-dimensional ultra-sound, or by measuring the temperature at discrete locations in-situ with thermo-couples or thermo-sensing fluorescent probes.

Intraoperative monitoring with MRI has numerous disadvantages which include being expensive and not being able to be used with metal protected light guides which are currently used for the LITT probe. Three-dimensional ultra-sound imaging techniques are currently at an experimental stage and have not been sufficiently developed. In situ thereto-couples or fluorescence-based temperature probes only provide temperatures at a relatively small number of points throughout the tissue being monitored. Currently, only fluorescence-based temperature probes are approved by the FDA for clinical use.

SUMMARY OF THE INVENTION

It is thus an object of this invention to provide an intraoperative monitoring device and method used in conjunction with diagnostic procedures.

It is another object of this invention to provide an intraoperative monitoring device and method used in conjunction with stereotactic X-ray mammography.

It is another object of this invention to provide an intraoperative monitoring method and device that provides a high resolution X-ray image of temperature-induced changes to tissue during thermotherapy.

It is another object of this invention to provide an intraoperative monitoring device and method that provides a high resolution temperature map of tissue during thermotherapy.

It is another object of this invention to provide a method of thermotherapy which includes real-time monitoring of temperature induced changes to tissue during thermotherapy using X-ray imaging for feedback information used during the thermotherapy.

The above, and related objects of this invention are realized by providing a device for monitoring thermally-induced changes to localized regions of tissue which has an X-ray illumination source, an X-ray detector, a data storage unit in communication with the X-ray detector, an image comparison unit in comparison with at least the data storage unit and an image display unit in communication with the image comparison unit. The X-ray illumination source and the X-ray detector are arranged to reserve a space therebetween for accommodating tissue to be monitored. Preferably, the tissue to be monitored is a portion of a patient's body which is being monitored during the surgical procedure. The X-ray detector produces a plurality of X-ray image data signals, each of which corresponds to an X-ray image of the portion of the patient's body being monitored. Preferably, the X-ray detector produces a digital X-ray image data signal. The X-ray image data signal corresponds to a two-dimensional image of the portion of the patient's body being monitored in a preferred embodiment, and corresponds to a three-dimensional X-ray image of the portion of the patient's body in another preferred embodiment.

The image comparison unit compares X-ray image values between corresponding spatial points of first and second X-ray image signals to provide a resultant X-ray image signal based on the comparison. Preferably, the image comparison unit subtracts pixel values between corresponding spatial points of first and second X-ray image signals, providing a measure of the change in intensity of the received X-ray signal at each point within the digital X-ray image signals. The resultant image signal is then one particular example of a difference image signal that is generated by the image comparison unit and then displayed on an image display unit to provide real-time information concerning the temperature distribution and changes in temperature throughout the portion of the patient's body being monitored. The images also provide information corresponding to the volume of denatured tissue. In the preferred embodiment, both the data storage unit and image comparison unit are implemented within a personal computer or workstation.

Another preferred embodiment of the present invention is directed to a device for causing thermally-induced changes to localized regions of tissue. The device according to this preferred embodiment has an X-ray illumination source, an X-ray detector, a data storage unit in communication with the X-ray detector, a thermotherapy heating assembly, an image comparison unit in communication with at least the data storage unit and an image display unit in communication with the image comparison unit. The combination of X-ray illumination source, X-ray detector, data storage unit, image comparison unit, and image display unit are constructed and arranged in a manner similar to the monitoring device summarized above. The thermotherapy heating assembly may be selected from currently known devices and may include a laser irradiation devices, microwave irradiation devices, radio frequency irradiation device, or an ultra-sound energy source. In the preferred embodiment, the thermotherapy heating assembly is a laser interstitial thermotherapy assembly. There are laser interstitial thermotherapy assemblies known in the art that are suitable for use with the device for causing thermally-induced changes to localized regions of tissue, in accordance with this invention. For example, the laser interstitial thermotherapy devices described in Robinson, David S. et al, "Interstitial Laser Hyperthermia Model Development for Minimally Invasive Therapy of Breast Carcinoma", *J. Am Coil Surg,* 1998, reprint pages 284-292; Milne, Peter J. et al, "Development of Stereotactically Guided Laser Interstitial Thermotherapy of Breast Cancer: In Situ Measurement and Analysis of the Temperature Field in Ex Vivo and In Vivo Adipose Tissue," 15 *Lasers in Surgery and Medicine,* 2000, reprint 26:67-75; and Maims, Fabrice et al, "In Situ Temperature Measurements With Thermocouple Probes During Laser Interstitial Thermotherapy (LTT): Quantification and Correction of a measurement Artifact," *Lasers in Surgery and Medicine,* Vol. 23, No. 2, 1998, reprint pages 94-103 are suitable: the entire content of each is incorporated herein by references.

Another preferred embodiment of this invention is directed to a method of thermally inducing and monitoring changes to localized regions of tissue, including illuminating a volume of tissue with a first beam of X-rays, detecting portions of the first beam of X-rays that pass through localized regions of tissue within the volume of tissue, generating a first X-ray image signal from the portions of the first X-ray beam detected, and applying heat to at least a localized region of tissue within the volume of tissue. A preferred embodiment of the method is directed to thermally inducing and monitoring changes to tumors in breast cancer patients. After applying the heat, the volume of tissue is illuminated with a second beam of X-rays. X-rays from a second beam of X-rays that pass through the volume of tissue that includes the localized regions, e.g., through the tumors, are detected and a second X-ray image signal is generated therefrom. In the preferred embodiment, the first X-ray image signal is stored in a data storage unit and then retrieved for generating a resultant image signal which preferably is a difference image signal based upon a comparison of the first and second X-ray image signals. In a preferred embodiment, the first and second X-ray image signals and the difference image signal are digital signals and the difference image signal is formed by subtracting each pixel value of the first X-ray image signal from a spatially corresponding pixel of the second X-ray image signal. Each X-ray image signal is correlated with the detected X-ray intensity corresponding to the particular spatial point, and the difference image signal corresponds to an intensity change in the detected X-rays for each corresponding difference image point. The difference image signal is rendered as a difference image and displayed on an image display device, preferably, to provide real-time feedback to the surgeon applying thermotherapy. The surgeon can then determine whether to alter the thermotherapy parameters, maintain the thermotherapy, or terminate the thermotherapy with the aid of the temperature change information displayed on the image display device.

If the surgeon decides to continue the thermotherapy, the volume of tissue is illuminated with a third beam of X-rays. (The X-ray beams may be along the same or modified paths relative to the volume of tissue.) The X-rays from the third beam that pass through the volume of tissue are detected and a third X-ray image signal is generated therefrom. The second and third beam of X-rays may be separated in time by a period in which there is no illumination of X-rays, or it may be a continuous illumination classified as contiguous time periods. Continuous illumination is currently less preferable than intermittent illumination due to safety concerns regarding the total X-ray dose applied to the patient.

The first X-ray image signal is again retrieved from the data storage unit and used as a static reference image signal to produce a second difference image signal by subtracting each corresponding pixel of the first and second image signals. The second difference image signal is then rendered and displayed as an updated difference image which provides updated information to the surgeon, preferably in real time. The surgeon can then use the temperature change information displayed to reassess the status of the thermotherapy to determine whether to alter, continue or terminate the thermotherapy.

This process is repeated until the surgeon determines that the thermotherapy should be terminated. In this embodiment, the difference image signal is always generated by retrieving the same static reference image signal from the data storage unit and subtracting it from the updated measurement signal.

The above detailed description of a succession of measurements is by way of example. The reader should recognize from the teachings herein that the scope and spirit of the invention includes the general concepts and not the particular order of observing and responding to the observations.

In an alternative embodiment, all method steps are the same as those 20 noted above, except that a static reference image signal is not used to generate the difference image signal. In this preferred embodiment, the first X-ray image signal is replaced by the second X-ray image signal after the first difference image signal is generated. Similarly, the second X-ray image signal stored in the data storage unit is replaced with the third X-ray image signal after the second difference image signal is generated. This process is repeated until the surgeon determines that the thermotherapy should be terminated. This case provides a dynamic reference image signal for forming the difference image signal in which the dynamic reference image signal is updated after each succeeding illumination.

In alternative embodiments, one may combine both static and dynamic processes for generating the difference image signals. For example, the reference image signal may be maintained in memory without being replaced for one, two or more successive illuminations, followed by being updated either frequently, such as with a pure dynamic reference image signal, or intermittently, again being a mix of dynamic and static processes.

Another embodiment of the invention is directed to a method of destroying cancerous tissue by forming a first X-ray image of a portion of a patient's body, applying heat to a localized region of the portion of the patient's body, forming a second X-ray image of the portion of the patient's body subsequent to applying heat to the localized region of the portion of the patient's body, and generating a difference image based on a comparison of the first X-ray image data to the second X-ray image data. The surgeon then modifies the application of heat based on information obtained from the difference image. In a preferred embodiment, the first and second X-ray images and the difference X-ray image are high resolution, three-dimensional digital X-ray images. Preferably, the comparison is a subtraction of the first X-ray image from the second X-ray image. The illumination with successive X-ray beams, detecting, generating X-ray image signals, and generating successive difference image signals is repeated as the surgeon requires until he terminates the thermotherapy.

BRIEF DESCRIPTION OF THE DRAWINGS

These and other objects and advantages of the invention will become more apparent and more readily appreciated, from the following detailed description of the presently preferred exemplary embodiments of the invention taken in conjunction with the accompanying drawings, of which:

FIG. 5 is a flowchart illustrating a preferred embodiment of a method according to this invention;

DETAILED DESCRIPTION OF THE PREFERRED EMBODIMENTS

Figure 1:
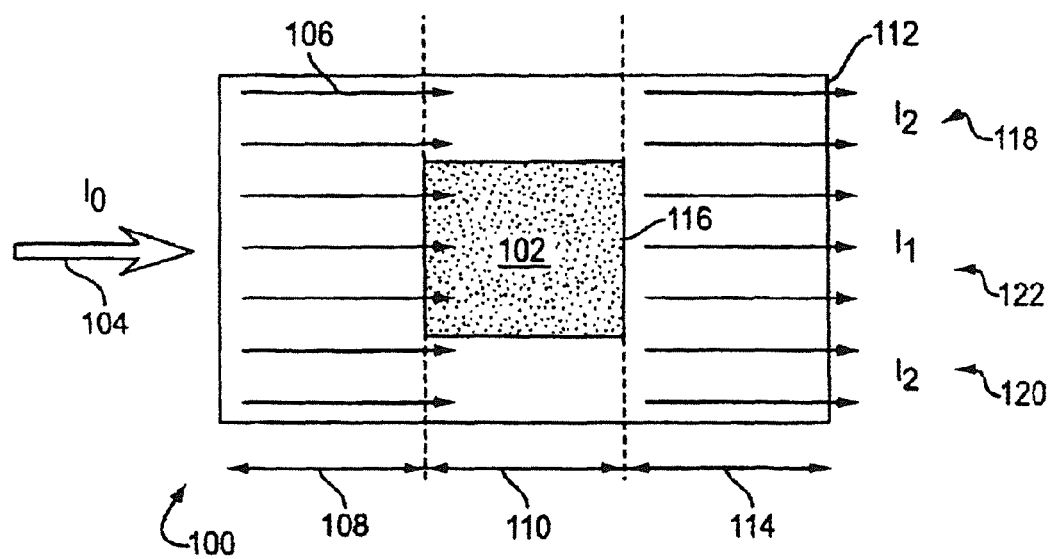
FIG. 1 is a schematic illustration for explaining general concepts of the invention.

We first explain the general concepts of the invention with reference to 20 FIG. 1. FIG. 1 is a schematic illustration of a volume of tissue 100 which contains a localized region of tissue 102. In the preferred embodiments, the localized region of tissue 102 is a tumor formed of cancerous tissue. The volume of tissue 100 is illuminated with a collimated beam of X-rays 104 illustrated schematically in FIG. 1 as a heavy arrow and also labeled $I_0$ representing the intensity of the collimated X-ray beam. The collimated X-ray beam 104 has a plurality of beam portions, one of which is labeled 106 in FIG. 1, that pass through a portion of the volume of tissue 100 for a distance 108 before reaching the depth of the tumor 102. The tumor 102 is represented as having a simple structure in FIG. 1 for the purpose of illustrating the general concept of the invention. For facilitating the explanation, the tumor 102 has a uniform thickness 110 along the direction of the path of the X-ray beam 104. In FIG. 1, the X-ray beam is illustrated as a collimated beam to facilitate the discussion. The X-ray beams emitted by sources currently used are diverging beams. Portions of the X-ray beam such as 106 pass through the volume of tissue 100 without passing through the 10 tumor 102 and emerge from the volume of tissue 100 at an opposing side 112 of the volume of tissue 100. Again, for facilitating the explanation of the general concepts of the invention, the volume of tissue 100 is also assumed to have a simple structure in which it has a uniform width which is the sum of the distances 108 to reach the tumor 102, plus the distance 110 in order to pass by or through the tumor 102, plus the distance 114 to pass from an opposing end 116 of the tumor 102 to exit the volume of tissue 100 at the opposing end 112 of the volume of tissue 100.

It is well established that electromagnetic radiation has a dual nature in which it can be thought of as a collection of a plurality of photons, or may be thought of as an electromagnetic wave or waves. The particle view is convenient to imagine that the X-ray beam is a collection of a large number of particles, i.e., photons, in which some of the plurality of photons traverse a path which misses the tumor 102, while another plurality of photons traverse a path through the volume of tissue 100 and then pass through the tumor 102. Photons traveling along a path 106 miss the tumor 102 and exit the volume of tissue 100 at the opposing end 112 after traveling through a distance of tissue which is the sum of the distances 108, plus 110, plus 114. In this illustrative example, the collection of all photons which pass above the tumor 102 in FIG. 1 and exit the opposing end 112 of the volume of tissue 100 together form an intensity sub-beam 118, as illustrated in FIG. 1, without passing through a tumor 102. Similarly, a portion of the X-ray beam 104 that passes through the volume of tissue 100 to emerge at the opposing end 112 below the tumor 102, as illustrated in FIG. 1, without passing through the tumor 102 forms a sub-beam intensity 120. A portion of the X-ray beam 104 which passes through a length of tissue 108 before reaching the tumor 102, and passes through the length 110 of tumor 102, followed by passing through another length of tissue 114, emerges as an X-ray beam component 122.

Conventional X-ray observation techniques rely on the fact that the tumor tissue 102 attenuates and/or absorbs X-rays more than the surrounding tissue in the volume of tissue 100. Consequently, if the X-ray beam 104 entering the volume 100 is uniform when it enters the volume, the beam portions 118 and 120 will be more intense than the beam portion 122, due to additional attenuation and/or absorption by the tumor 102. The inventors recognized that the temperature-dependent attenuation and/or absorption of X-rays by tissue can be utilized to provide improved diagnostic methods and devices as well as to provide methods and devices for a combination of therapeutic and diagnostic techniques.

The above-described schematic illustration can also be modeled mathematically. The incident intensity is represented as Io and the detected intensity at a position x, y, in the plane perpendicular to the figure at opposing end 112 of the volume of tissue 100, is represented as $$I_d(x,y) = I_0 e^{-\int \mu(x,y,z)dz} \quad (1)$$

where $\mu(x,y,z)$ is the attenuation coefficient at each three-dimensional point within the volume of tissue.

Upon selecting a coordinate system in which the plane orthogonal to the plane of FIG. 1 at the opposing end 112 of the volume of tissue 100 is an X-Y plane and the Z-direction is the direction of travel of the X-ray beam, the lengths 108, 110 and 114 are represented as $z_1$, $z_2$ and $z_3$, respectively. In the model illustrated in FIG. 1, a photon passing along the line 106 and exiting the volume of tissue 100 at the opposing end 112 is assumed to traverse a substantially homogeneous region of tissue in which the attenuation coefficient is constant in the Z-direction, and represented by~The intensity of X-rays passing through a portion of the volume of tissue 100 within the region 118 is then represented as $$I_2 = I_0 e^{-\mu_1(z_1+z_2+z_3)} \quad (2)$$

where the integration performed along the Z-direction leads to the factor $z_1+z_2+z_3$ in the exponential which is simply the total distance traveled through the volume of tissue 100 in the Z-direction. Similarly, the intensity of X-rays emerging at the region 122 that pass through two regions of normal tissue, as well as passing through the tumor, is represented as $$I_1' = I_0 e^{-\mu_1(z_1+z_3)-\mu_2 z_2} \quad (3)$$

Where $\mu_2$ is the attenuation coefficient within the tumor which is substantially constant along the Z-direction, the attenuation coefficient $\mu_2$ is generally different from the attenuation coefficient $\mu_1$.

Generally, the tumor 102 attenuates X-rays more than that of surrounding healthy tissue. This is the case when the tumor is breast cancer. In that case, to a first approximation, one can assume that the healthy tissue causes essentially no attenuation to the beam of X-rays, while X-rays passing through the tumor are attenuated more strongly. In this approximation, equations 2 and 3 become $$I_2 = I_0 \quad (4)$$

$$I_1 = I_0 e^{-\mu_0 z_2} e^{-bT z_2} \quad (5)$$

respectively.

The inventors recognized that certain types of tissue have a temperature variation in its attenuation of X-rays. This can be represented in the above-noted illustrative model by an attenuation coefficient which varies with temperature. For example, a linear variation with temperature of the temperature coefficient $\mu = \mu_0 + bT$ leads to a temperature-dependent intensity $$I_1(T) = I_0 e^{-\mu_0 z_2} e^{-bT z_2} \quad (6)$$

at the region 122. As one can see from equation 6, the intensity I~varies with temperature. If there was no variation in X-ray attenuation properties of the tumor with respect to changes in temperature, then b would be equal to zero, and the second factor in equation 6 would be equal to unity. In that case, comparing the intensity of X-rays sent through the tumor at different temperatures would lead to substantially the same intensity. However, since there is a temperature variation in the attenuation properties of X-rays by the tumor, the intensity according to equation 6 at a temperature $T_1$ is different from that of another temperature $T_2$. This temperature-dependent variation in X-ray attenuation by the tumor can be exploited by observing the change in intensity I~as the temperature changes. For example, the ratio of the intensity at temperature $T_2$ to the intensity at temperature $T_1$, according to equation 6 can be represented as $$\frac{I_1(T_2)}{I_1(T_1)} = e^{-bz_2(T_2-T_1)} \quad (7)$$

If there were no temperature variation in the X-ray attenuation coefficient of the tumor 102, equation 7 would be equal to unity. The deviations from unity signify the temperature variations in the intensity of X-rays passing through the tumor 102. The ratio of intensities in this case is taken as a measure to recognize the change in intensity of X-rays passing through the tumor 102 with changes in temperature. However, the invention includes generally comparing the changes in intensity of X-rays passing through tumors that are correlated with changes in temperature and changes induced by temperature. For example, another useful method of comparing the changes of intensity of X-rays passing through the tumor with changes in temperature is to subtract the intensity values. There are innumerable measures that one may use to implement the general concept of comparing the intensity of X-rays passing through the tumor at one temperature to the intensity of X-rays passing through the tumor at another temperature.

This invention is directed generally to the concept of utilizing such a change in X-ray intensity with a change in temperature in methods and devices.

The following detailed description of the preferred embodiments of the methods and apparatuses of this invention will refer particularly to the application of laser interstitial thermotherapy (LITT) which is a surgical procedure for the treatment of cancer tumors where near infra-red laser energy is delivered to the tumor site inside the body through a flexible fiber-optic probe that has a light diffusing tip. The inventors have found that the temperature increase generated during LITT will cause a change in the X-ray density of the heated tissue which is detectable in accordance with this invention. In addition, thermal denaturation causes a variation in tissue X-ray density which is detectable according to this invention. The LITT procedure will be described in detail in the preferred embodiment; however, the general concepts of the invention include other mechanisms now known, and later developed which lead to heating tumor tissue. For example, lasers which irradiate tissue with electromagnetic radiation in regions other than the near infra-red region, microwave sources of radiation, radio frequency sources, and ultra-sound energy sources are all mechanisms that can be used to heat tumor tissue. Furthermore, the heat sources may be internally applied heat sources such as the LITT method, or they may be external sources.

In addition, the preferred embodiments describe applications to breast cancer in particular detail. However, it is anticipated that other forms of tissue monitoring and treatment is included within the general concept of the invention. For example, the inventors anticipate that choroidal tumors of the eye, prostate cancer, and liver cancer are also particularly suitable for tumor monitoring and treatment according to this invention. The inventors anticipate that this invention is generally applicable to monitoring temperature changes in localized regions of tissue whenever the localized regions of tissue have a temperature variation in X-ray attenuation compared to a surrounding volume of tissue.

Figure 2:
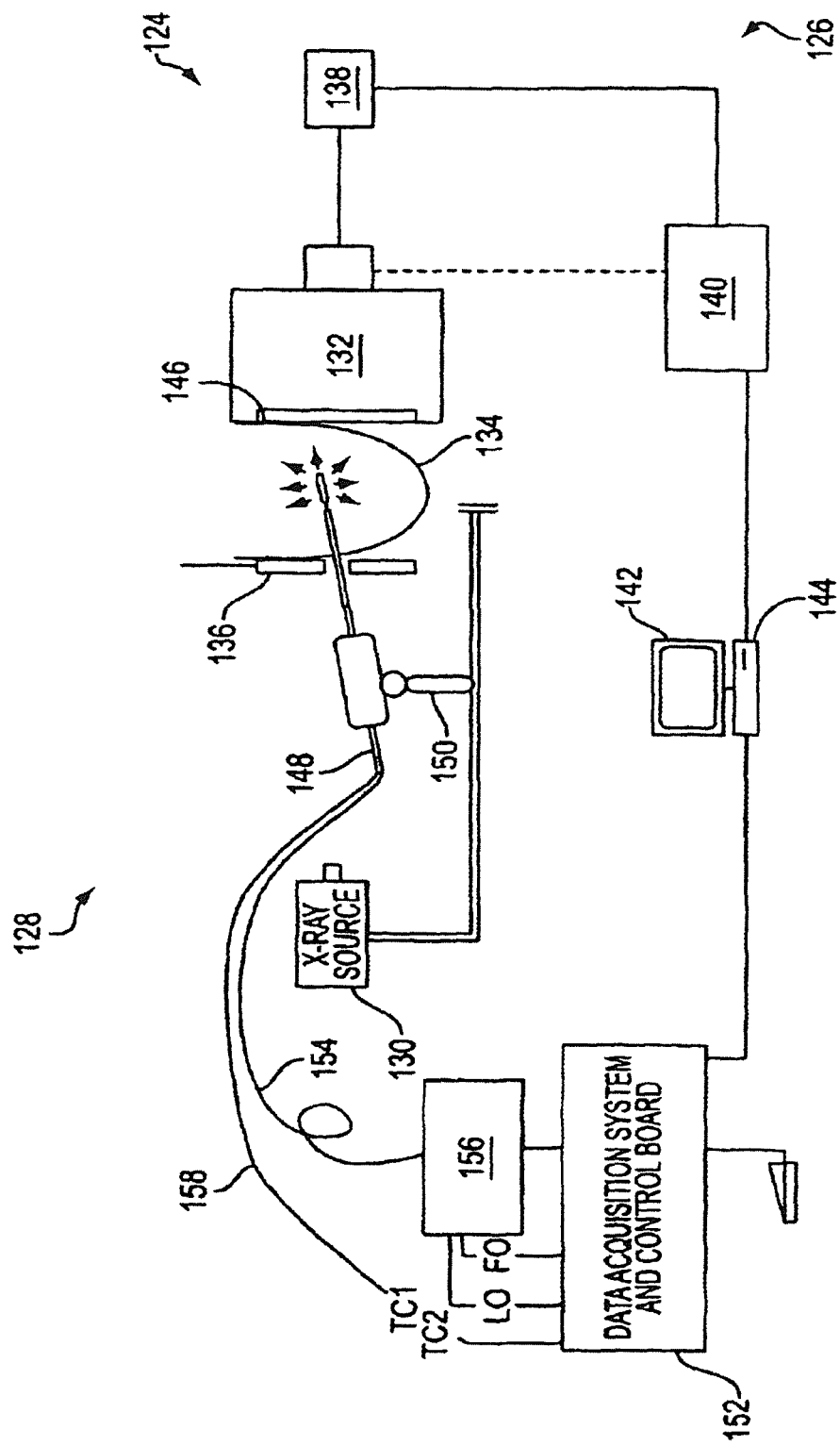
FIG. 2 is a schematic illustration of a device for causing and monitoring thermally induced changes to localized regions of tissue in accordance with a preferred embodiment of the invention.

An example of a thermal therapy device in accordance with a preferred embodiment of this invention is illustrated in FIG. 2, and labeled generally by reference numeral 124. The thermal therapy device 124 has a monitoring unit 126 and a heating assembly 128. The monitoring unit 126 has an X-ray illumination source 130 and an X-ray detector 132 disposed proximate to the X-ray illumination source 130. A space is reserved between an X-ray illumination source 130 and X-ray detector 132 for accommodating tissue to be monitored, and/or treated, such as a portion of a person's body. In the example illustrated in FIG. 2, a woman's breast 134 is arranged between the X-ray illumination source 130 and the X-ray detector 132 for the treatment and treatment monitoring of breast cancer. A compression plate 136 compresses the patient's breast 134 in contact with the X-ray detector 132. The monitoring unit 126 has a data storage unit 138 that is in communication with the X-ray detector 132. The monitoring unit 126 also has an image comparison unit 140 that is in communication with at least the data storage unit 138 (see, the dashed line in FIG. 2). In an embodiment of the invention, the image comparison unit 140 is in communication with both the X-ray detector 132 and the data storage unit 138. The image comparison unit 140 is in communication with an image display unit 142. The image display unit 142 may be a separate specially designed display unit, or may be the monitor of a personal computer or workstation 144. Each of the image comparison unit 140 and data storage unit 138 maybe separate dedicated components, or may be implemented on the personal computer or workstation. Furthermore, the image comparison unit 140 maybe a stand-alone special function component, or may be implemented by programming the personal computer 144. Special function stand-alone units typically allow one to optimize performance, but at a higher cost.

In the preferred embodiment, the X-ray detector 132 is a digital detector that produces a digital X-ray image signal. The invention is not limited to digital X-ray detectors, and includes analog detectors producing analog X-ray image signals. In the preferred embodiment, the X-ray detector 132 has a fluorescent screen 146 which fluoresces in the visible region of the electromagnetic spectrum upon being struck by X-rays from X-ray illumination source 130.

The light emitted by the fluorescent screen is detected by an array of CCD elements in the preferred embodiment. Furthermore, a preferred embodiment will typically have optical components arranged between the fluorescent screen and the CCD array (not shown in the drawings) in order to condense and focus the fluorescing light onto the CCD detector. There are high-resolution digital X-ray imaging devices currently on the market for treating and monitoring breast cancer which are suitable for use according to this invention. Preferably, the monitoring unit 126 employs a three-dimensional X-ray imaging system, such as stereotactic X-ray imaging. The MAMMOVISION~system 85200G-2 produced by Fischer Imaging Company was found to be suitable for use in the monitoring unit 126. The U.S. Pat. Nos. 5,078,142; 5,365,562; 5,526,394; and 5,917,881, each of which is incorporated by reference herein in their entirety, describe details of various aspects of X-ray imaging systems suitable for application in the monitoring unit 126.

Figure 4:
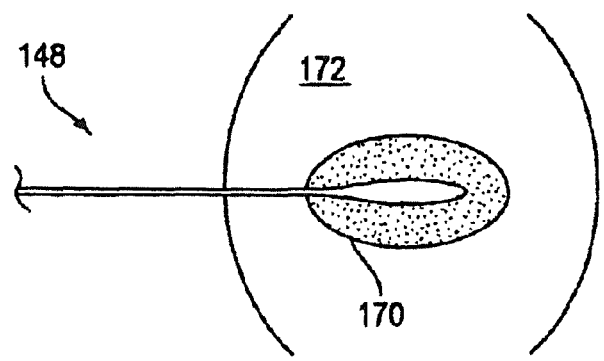
FIG. 4 is a schematic illustration of applying heat to a tumor in accordance with the preferred embodiment of this invention.
Figures 3A, 3B:
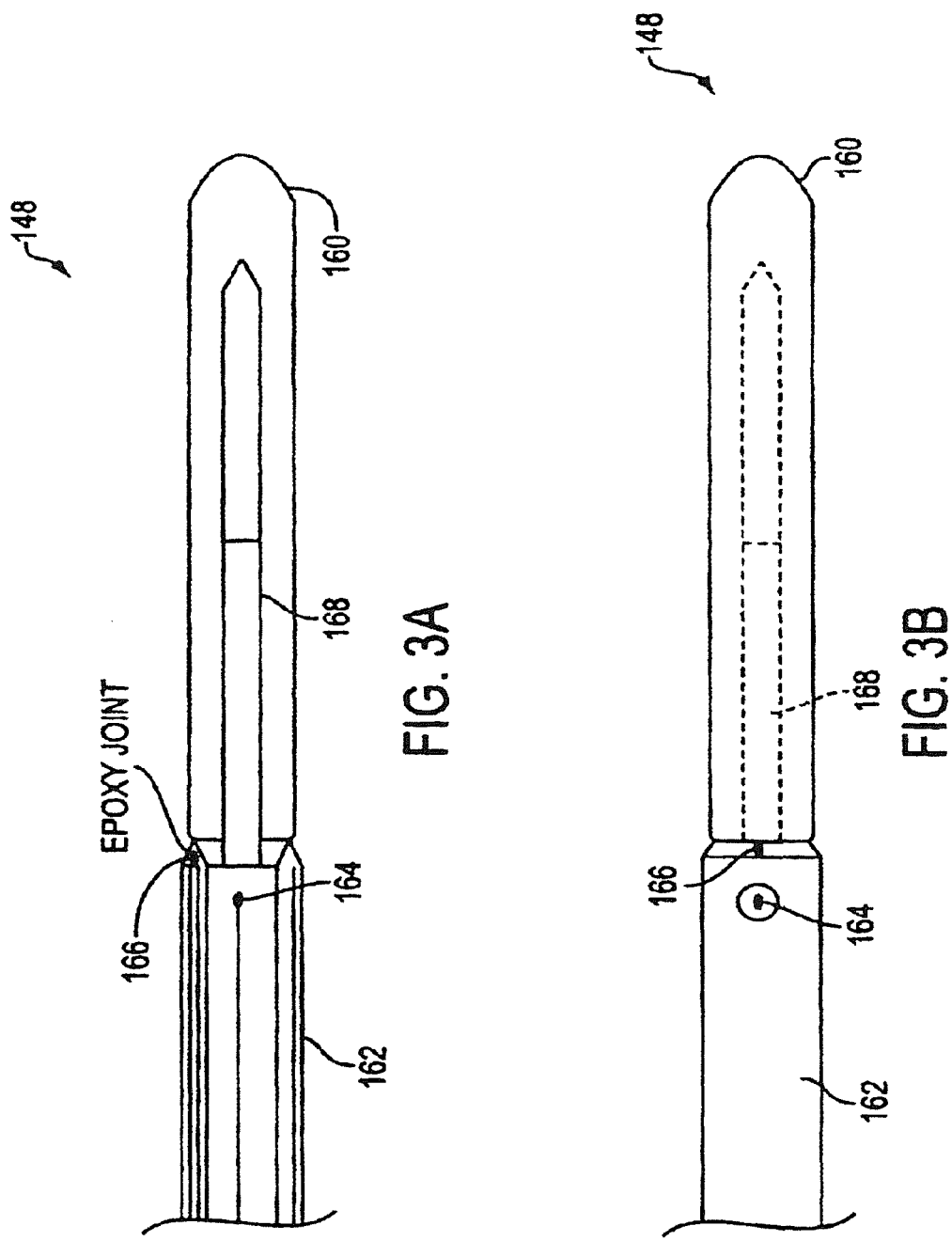
FIG. 3A is a partially cut-away view of a probe within a heating 5 assembly in a preferred embodiment of this invention.
FIG. 3B is a side view of an end of the probe illustrated in FIG. 3A.

In the preferred embodiment, the heating assembly 128 is a laser interstitial thermal therapy assembly. The LITT assembly 128 has a MAMMOGRAPHIC thermal ablative therapy probe 148 attached to sled 150 which is controlled by a data acquisition system and control unit 152. An optical fiber 154 attached to the probe 148 to transport the laser energy from the laser 156. In a preferred embodiment, the laser is a continuous wave Nd:YAG laser. The invention anticipates that other lasers such as semiconductor lasers and gas lasers will be used in particular applications. Furthermore, it is anticipated that pulsed lasers may be suitable in some applications. The LITT assembly 128 also has a plurality of thermocouples 158. The insertion portion of the probe 148 is shown in more detail in FIGS. 3A and 3B. The outer layers of the probe 148 are cut-away in cross-section in FIG. 3A to show a cross-sectional view of the quartz diffusing cap 160 and a cross-sectional view of the stainless steel tube 162. The probe 148 has two thermocouples 164 and 166, respectively. The optical fibre 168 is exposed in the cut-away view of the quartz diffusing cap 160 and stainless steel tube 162. FIG. 3B shows a side view corresponding to FIG. 3A. FIG. 4 is a schematic illustration of the probe 148 inserted into a tumor 170 within a surrounding volume of tissue 172.

FIG. 5 illustrates a preferred embodiment of a method of thermally inducing and monitoring changes to localized regions of tissue, in accordance with the invention. A region of tissue 134 arranged between the X-ray illumination source 130 and the X-ray detector 142 is illuminated with a first beam of X-rays (see, FIG. 2 in conjunction with FIG. 5). The X-ray detector 132 detects a plurality of portions of the first beam of X-rays after they have passed through the volume of tissue 134. The X-ray detector 132 generates a first X-ray image signal from a plurality of portions of X-rays detected from the first beam of X-rays. In a preferred embodiment, the first X-ray image signal is a digital signal. However, the general concept of the invention includes generating an analog X-ray image signal, rather than a digital X-ray image signal.

In a first preferred embodiment of a method of thermally inducing and monitoring changes to localized regions of tissue in accordance with the invention, the first X-ray image signal generated is a static reference X-ray image signal which is stored in a data storage unit 138 for later retrieval.

Heat is then applied to the tissue using an appropriate heating assembly for thermal therapy. For example, heat may be applied with the LITT assembly 128 illustrated in FIG. 2. However, as noted above, the heat application assembly may be selected according to the particular use from known heating assemblies such as various laser assemblies, microwave heating, radio frequency heating or ultrasound heating assemblies.

The tissue 134 is then illuminated with a second beam of X-rays at a second time. The X-ray detector 132 detects a plurality of portions of the second beam of X-rays that pass through the volume of tissue from the second beam of X-rays. The X-ray detector generates a second X-ray image signal from the plurality of portions of the second X-ray beam detected, which is preferably a digital X-ray image signal.

A resultant image signal is generated based upon a comparison between the first and second X-ray image signals generated. In a preferred embodiment, the resultant image signal is a difference image signal generated by subtracting each pixel of image data of the first digital X-ray image signal from each corresponding pixel of the second digital X-ray image signal. When the digital X-ray image signals are rendered as two-dimensional, and/or three-dimensional images, the pixel-by-pixel subtraction will correspond to subtractions at the same spatial location within the corresponding two-dimensional and/or three-dimensional image. Although the difference image signal generated is based upon a subtraction of image values in the preferred embodiment, the general concept of the invention is not limited to only subtracting image values. For example, a ratio between corresponding values could be taken, or innumerable other mathematical operations could be performed, as suitable, such as dividing all values by a normalization factor, etc. Furthermore groups of pixels may first be combined in various ways, such as pixel averaging prior to the generating a difference image signal. The image may be preprocessed by two-dimensional and/or three-dimensional Fourier transformation and comparing the images in the spatial-frequency domain either with or without prior spatial filtering.

The difference image signal is rendered as an image, preferably rendered as a real-time image on a display screen to provide information during thermal therapy. The displayed image of the difference signal provides information on the size and/or volume of localized regions of tissue, such as denatured tissue, as well as the rate of temperature changes or temperature-induced changes and the corresponding relative temperatures. The user may employ the displayed information to determine whether desired regions of tissue are receiving enough, or too much, heat, as well as determining the extent of tissue necrosis due to the thermal therapy. The displayed image may be utilized by the user to determine whether to continue the thermal therapy and to determine whether the heat application parameters need to be altered. For example, the amount of heat applied may be increased, or decreased, or the location where the heat is being applied may be altered.

If the user determines that the thermal therapy should continue, heat is again applied to the tissue. The heat application may be a continuous process in which the successive applications of heat may be considered to be contiguous time intervals. Alternatively, the heat may be applied in separate intervals, separated by periods in which no heat is applied to the tissue by the heat application assembly.

The region of tissue is then illuminated with another beam of X-rays in which portions are detected by the X-ray detector after they pass through the tissue. The beams of X-rays illuminating the tissue may be discrete illumination periods separated by non-illumination periods, or may be contiguous time periods forming a continuous illumination by X-rays classified in time intervals. The X-rays detected after the third illumination beam of X-rays lead to a third digital X-ray image signal generated according to the preferred embodiment of the invention. The same reference X-ray signal is retrieved from the data storage unit as was previously retrieved from the data storage unit. In this embodiment of the invention, the same reference X-ray image signal is used to generate difference image signals a plurality of times. This reference X-ray signal is thus called a static reference X-ray signal to indicate that it will remain unchanged for at least a plurality of difference image signals generated.

After retrieving the static reference X-ray image signal from the data 20 storage unit and generating a second resultant image signal, preferably a difference image signal, it is then rendered on a display screen. In the preferred embodiment, the user has the displayed image available to update determinations on size and/or volume of the cancerous and/or necrotic tissue as well as a temperature map, or map of temperature-induced changes, and temperature change map within the tissue area of observation. This process may then be repeated numerous times until the surgeon determines that the thermal therapy should be terminated.

The general concepts of the invention include generating both two-dimensional, and three-dimensional X-ray image signals (e.g., stereotactic X ray imaging), and generating the corresponding resultant X-ray image signals. In a preferred embodiment, three-dimensional X-ray image signals are produced. In the case in which three-dimensional image signals are produced by geometric triangulation methods, at least two X-ray beams through a given point within the illumination tissue must be detected. In order to obtain such data, the X-ray illumination source and/or detector may be moved relative to a tissue being illuminated, or there may be a plurality of illumination sources and/or X-ray detection elements.

Figure 6:
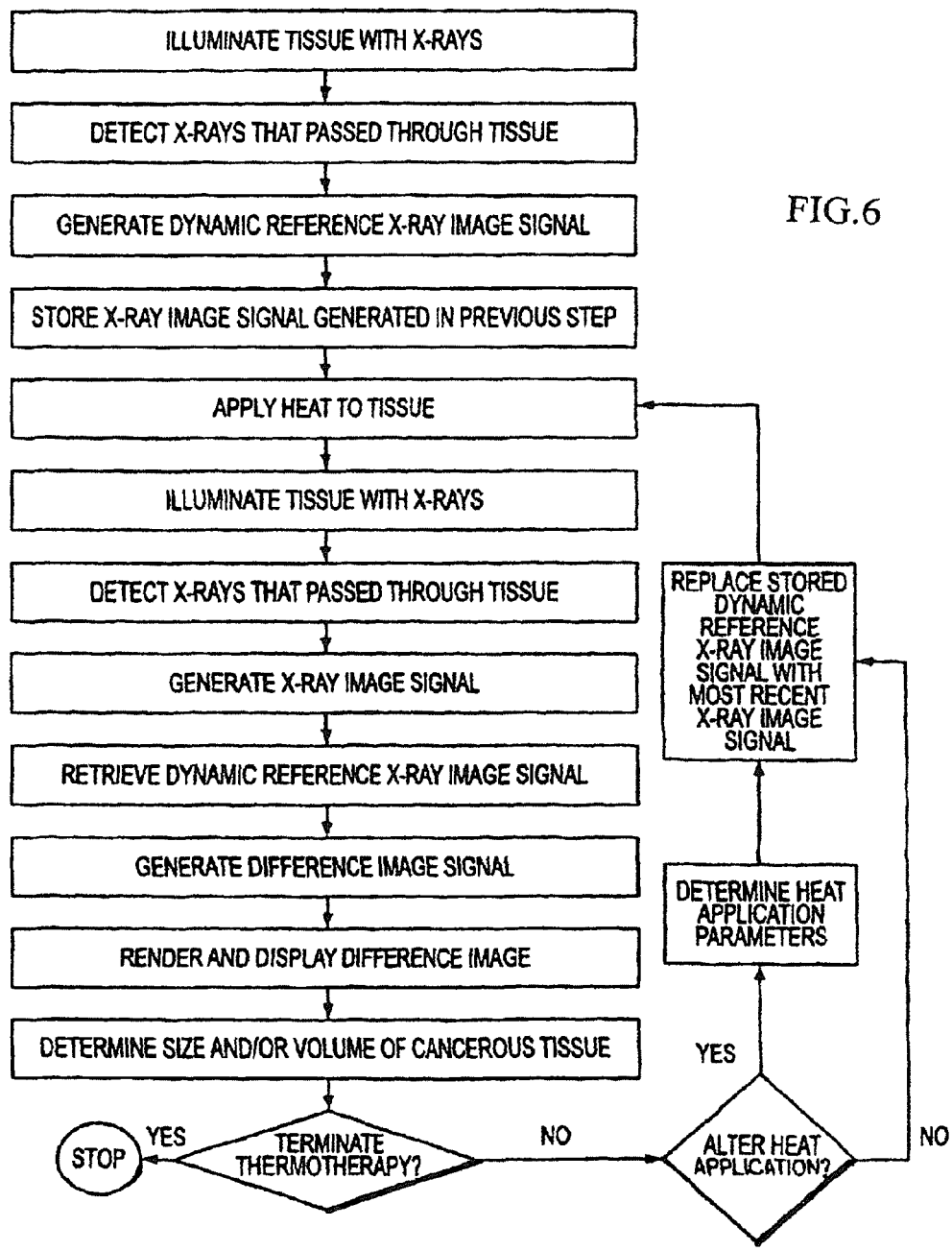
FIG. 6 is a flowchart illustrating another preferred embodiment of a method according to the invention.

FIG. 6 illustrates another preferred embodiment of a method of 10 thermally inducing and monitoring changes to localized regions of tissue in accordance with the invention. The description of the method of the preferred embodiment in FIG. 5 carries over to many of the steps illustrated in FIG. 6. In the embodiment of FIG. 6, the reference signal generated and stored in the data storage unit is a dynamic reference signal which is updated subsequent to each resultant image signal that is generated. After generating the resultant image signal, rendering and displaying the resultant image, determining the physical properties of the localized regions of tissue, and deciding to continue with thermal therapy, the second X-ray image signal replaces the first X-ray image signal in the data storage unit to become the up-dated dynamic reference signal. Heat is then applied to the tissue, followed by illumination of the tissue with a third beam of X-rays. The third beam of X-rays is detected after passing through the tissue illuminated with the X-rays, and a third X-ray signal is generated. The dynamic reference X-ray image signal is retrieved from the data storage unit and subtracted, pixel by pixel, from the third X-ray image signal to generate a second difference image signal. The second difference image signal is rendered and displayed on a display unit for a user to determine the various physical properties of the localized regions of tissue. If the surgeon determines that thermal therapy should continue, the third X-ray image signal replaces the previously X-ray signal in the data storage unit to become the up-dated dynamic reference image signal. This process is continued repeatedly until the surgeon determines that thermal therapy should be terminated.

The preferred embodiments illustrated in FIGS. 5 and 6 describe using either a static reference X-ray image signal, or a dynamic reference X-ray image signal. The general concept of the invention includes a combination of both static and reference image signals in which the reference signal may be static for a period of time, dynamically updated and then could become static again to provide an unlimited range of possible combinations between the two limits.

The following subsections describe several experiments conducted with apparatuses and methods according to the concepts and embodiments of this invention.

Mammovision Exposure Experiments on Laser Treatment of Porcine Tissue

This subsection describes preliminary imaging experiments using the MAMMOVISION System (85200G-2, Fischer Imaging Co. Denver, Colo.) during laser-irradiation of porcine fatty tissue with a 980 nm diode laser (AOC 25, AOC Medical Systems, South Plainfield, N.J.).

The Experimental Method:

A 20×8×3 cm piece of fatty porcine tissue with the skin was compressed at room temperature of 25° C. with the MAMMOVISION compression paddle. In a first experiment, an optical fiber with a diffusing tip with a diameter of 1.7 mm (REM series B) was inserted in the tissue after making a path with a stainless steel trocar. After the initial scout and stereo images were taken to ensure that the fiber was within view of the camera, we began the auto-firing sequence. The sequence was set to take exposures every 30 seconds, although the system actually took exposures every 32 seconds. The generator settings were 25 kV, 100 mA, and 90 mAs. The laser was fired continuously at 10 W starting after the first auto-firing exposure for approximately 9 minutes. After approximately 2 minutes, we moved the fiber back so that the tip would appear in the images. After the 18th exposure we turned off the laser and continued to take exposures for 2 minutes.

In a second experiment a bare fiber with a 0.6 mm diameter was used (3M series B). The experimental procedure was the same as with the diffusing fiber. The generator settings were 25 kV, 100 mA, and 50 mAs. The laser was fired from between the third and 15th exposures and again took images for two minutes of the cooling down period. It should also be noted that we varied the laser power from 5 to 10 W after one minute and from 10 to 15 W after another two minutes.

In order to measure quantitatively the difference between the exposures, the average intensity (in arbitrary units corresponding to X-ray density) in a region of interest surrounding the optical fibers (~30×20 mm for the diffusing tip and ~26× 18 mm for the bare fiber) was recorded for each image.

Figure 7:
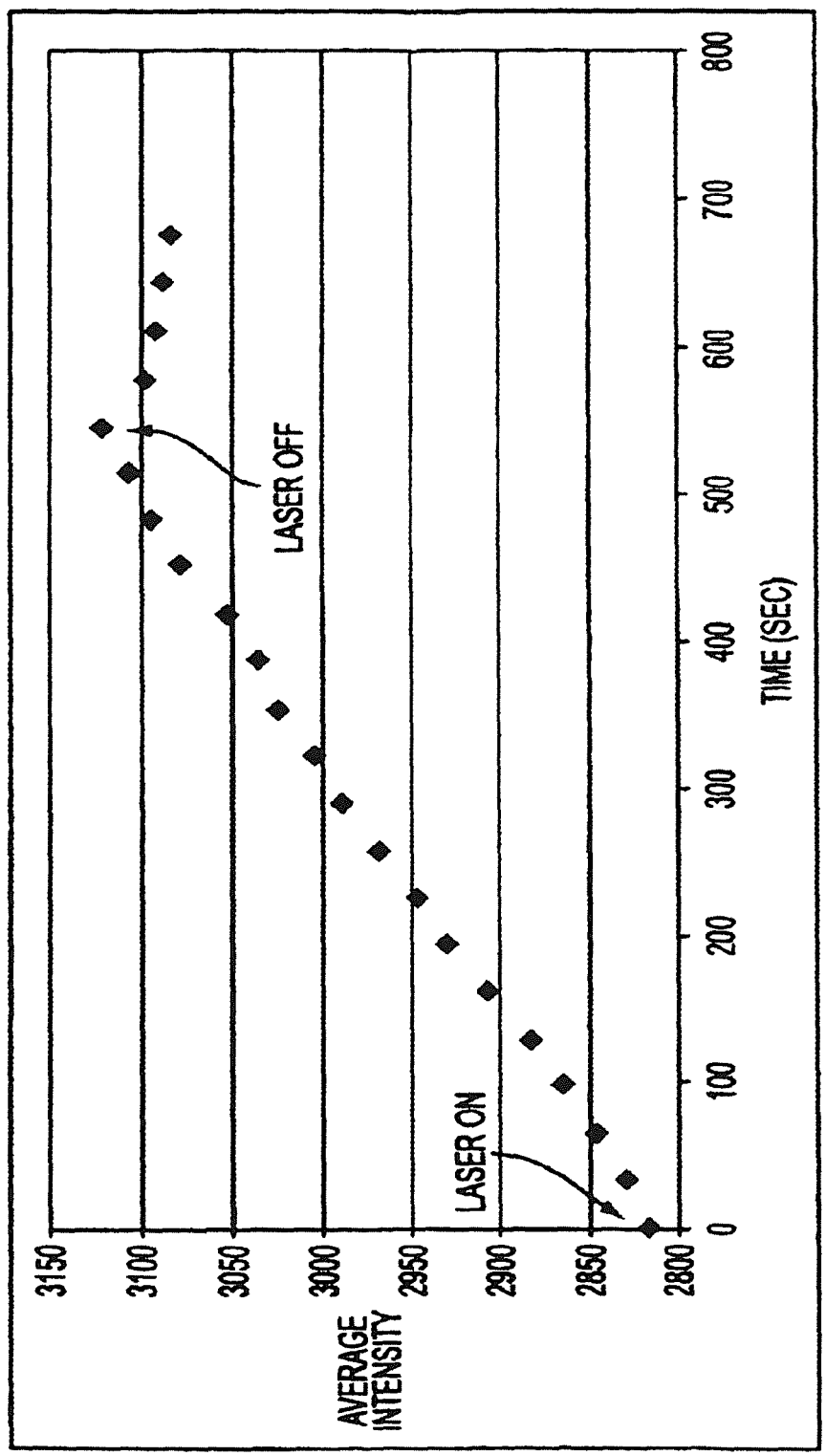
FIG. 7 is a graph showing average X-ray intensity in the region of 15 interest (diffusing fiber experiment)
Figure 8:
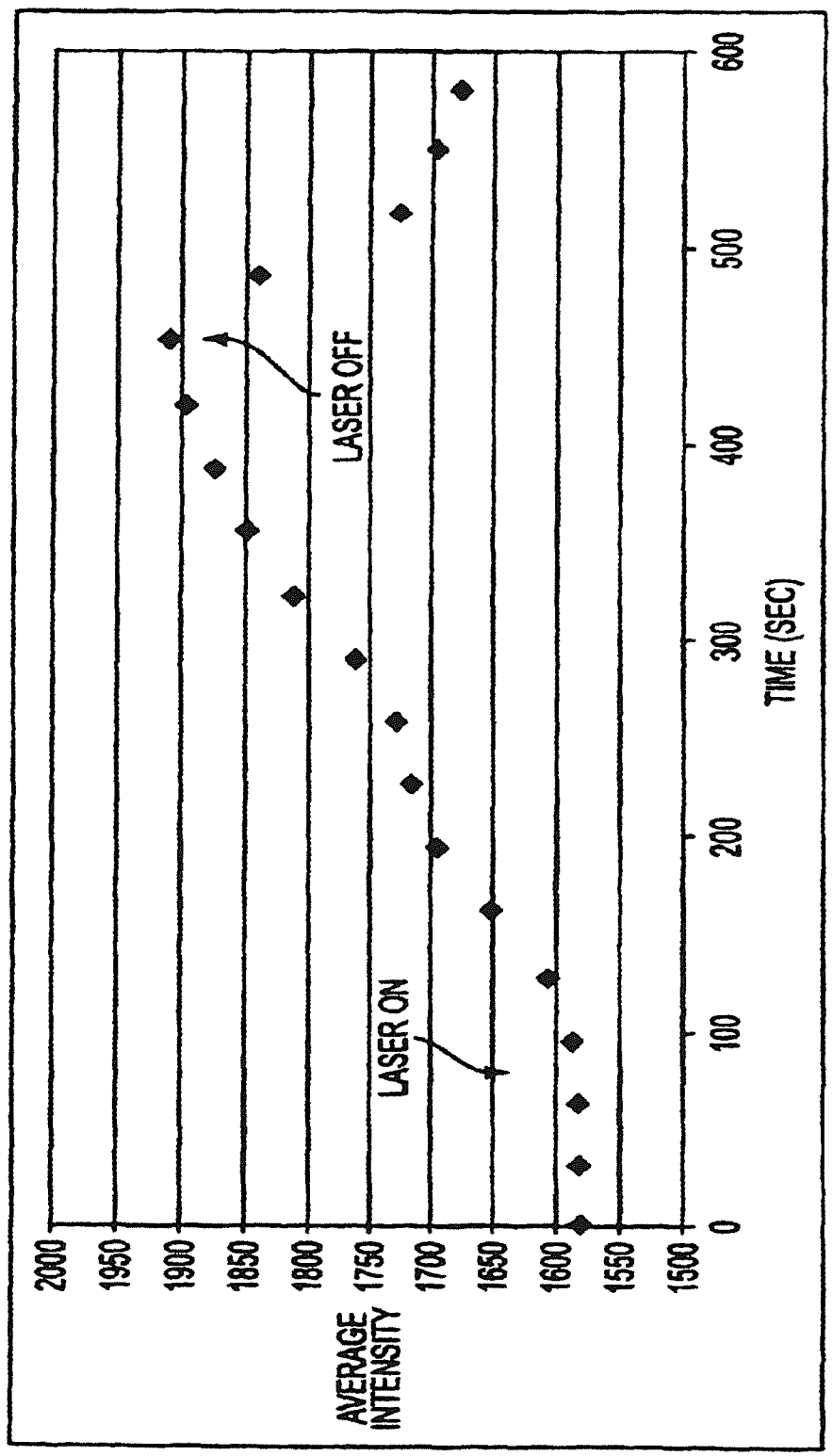
FIG. 8 is a graph showing average X-ray intensity in the region of interest (bare fiber experiment)

Results and Conclusion:

The average intensity of the region of interest increases approximately linearly during laser treatment of the tissue (FIGS. 7 and 8). The rates at which the average intensity increases are 34 units/mm for the diffusing tip experiment and 54 units/mm for the bare fiber experiment. After stopping the laser, the average intensities of the regions of interest decrease, although not to their initial levels. Both the average intensity increase during laser treatment and the decrease after laser treatment are higher in the bare fiber experiment.

Note:

The increases in the average intensity may either be a result of changes in the tissue density or to the camera's sensitivity to heat.

Continuation of Mammovision Exposure Experiments On Laser Treatment of Porcine Tissue This section describes a continuation of the preliminary imaging experiments with the MAMMOVISION System (85200G-2, Fischer Imaging Co., Denver, Colo.) during laser irradiation of fatty porcine tissue with a 980 nm diode laser (AOC 25, AOC Medical Systems, South Plainfield, N.J.).

The Experimental Method:

A 20×8×3 cm piece of fatty porcine tissue with the skin was compressed at room temperature of 25° C. with the MAMMOVISION compression paddle. An optical fiber (REM Series B) with a diffusing tip of diameter 1.7 mm was inserted in the tissue after making a path with a stainless 15 steel trocar (2.1 mm diameter). The laser was fired for 6 minutes at 10 W after the first image was taken and turned off for the remainder of the experiment.

After the initial stereo images were taken to ensure that the fiber was within view of the camera, we began the auto-firing sequence. The sequence was set to take images ever 30 seconds for the first 30 exposures, although the 20 system actually took exposures every 32 seconds. At this point (approximately minutes into the experiment), the auto-firing sequence was set to take exposures every 6 seconds.

Figure 9:
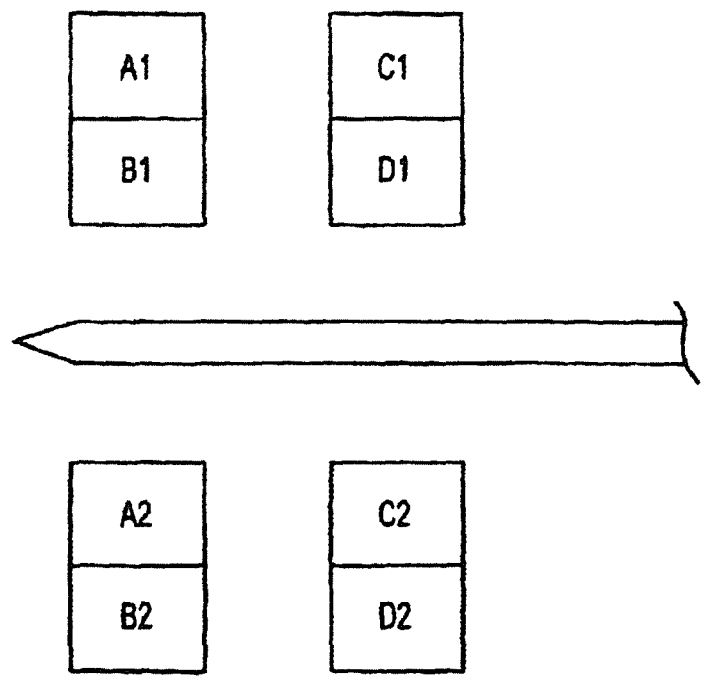
FIG. 9 is a schematic illustration of the region of interest with respect to a thermotherapy probe for the experiments of FIGS. 7 and 8.

The difference between the exposures was measured quantitatively by obtaining the average intensity (in arbitrary units corresponding to the optical density) in different regions of interests above and below the optical fiber 148 (see, FIG. 9). Regions directly surrounding the fiber were not studied because the fiber appears to shift through the images and its appearance in a region where it was not initially placed would skew the average intensity.

Results:

The following graphs in FIG. 10 illustrate the average intensity increases during the firing of the laser (the first six minutes) and decrease and level off during the remainder of the experiment. In general, the regions closer to the optical fiber show a more significant increase in average intensity during the laser irradiation than the regions further away.

Conclusion:

Although the fluctuations in average intensities of the regions of interest appear small, the increases correspond with the time that the laser is on. This suggests that the increase in average intensity is correlated to the laser irradiation (possibly by its thermal effects). Since the regions further away from the optical fiber show smaller increases than the closer regions, it appears that the effect of the laser irradiation on the tissue decreases with distance. The average intensities decrease after the laser is stopped and eventually level off. This may be caused by the temperature in the tissue dropping after irradiation and reaching an equilibrium.

Mammovision Exposure Stability Experiments of the PMMA Calibration Phantom

This subsection describes stability experiments conducted with the MAMMOVISION System (85200G-2, Fischer Imaging Co., Denver, Colo.) on the PMMA calibration phantom (10×10×4 cm) studied to determine if there are changes in average intensity of the 50×50 mm images produced by the CCD camera with time during the auto-firing sequence. The effect of an additional PMMA plate behind the calibration phantom is also presented.

The Experimental Method:

The 10×10×4 cm PMMA calibration block at room temperature (25° C.) was held in place before the MAMMOTEST camera with the compression paddle. In a first experiment, the auto-firing sequence was set to 5 take exposures every 30 seconds for approximately 15 minutes (after the initial scout and stereo images were taken). The initial scout was taken in the Autoexposure mode and its parameters were used in the sequential firing. The generator was set manually at 25 kV, 280 mAs, and 100 mA for the sequential firing. The first image was accidentally taken at automatic generator settings and was not included in the data discussed below. In the second experiment, the auto-firing sequence was set to take exposures every 6 seconds for 3 minutes. The generator settings were set manually at 26 kV, 280 mAs, 100 mA.

Figure 11:
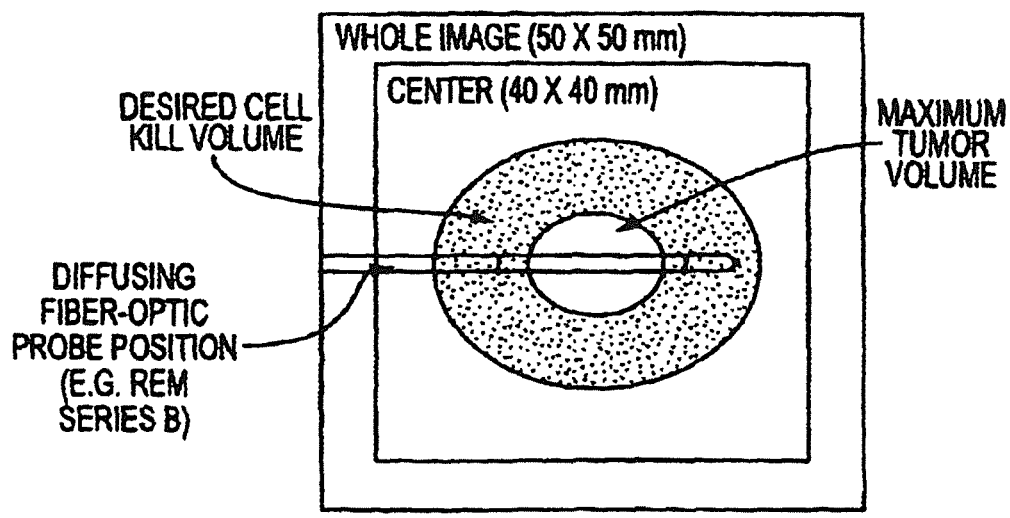
FIG. 11 illustrates desired hypothemiic effects in accordance with the invention.
Figure 10A:
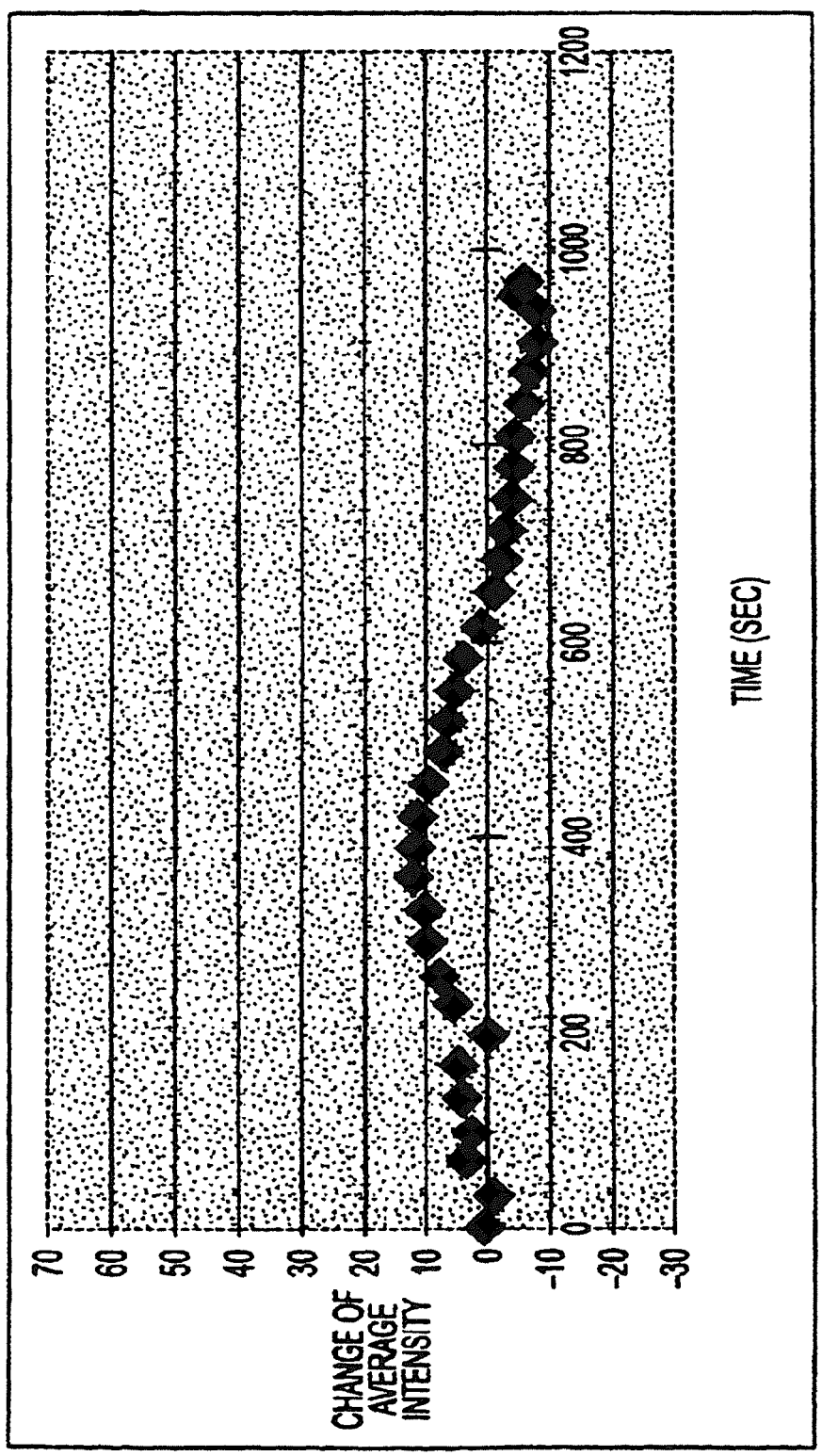
FIG. 10 shows graphs of changes of average X-ray intensity as a function of time for experimental regions of interest as illustrated in FIG. 9.
Figure 10B:
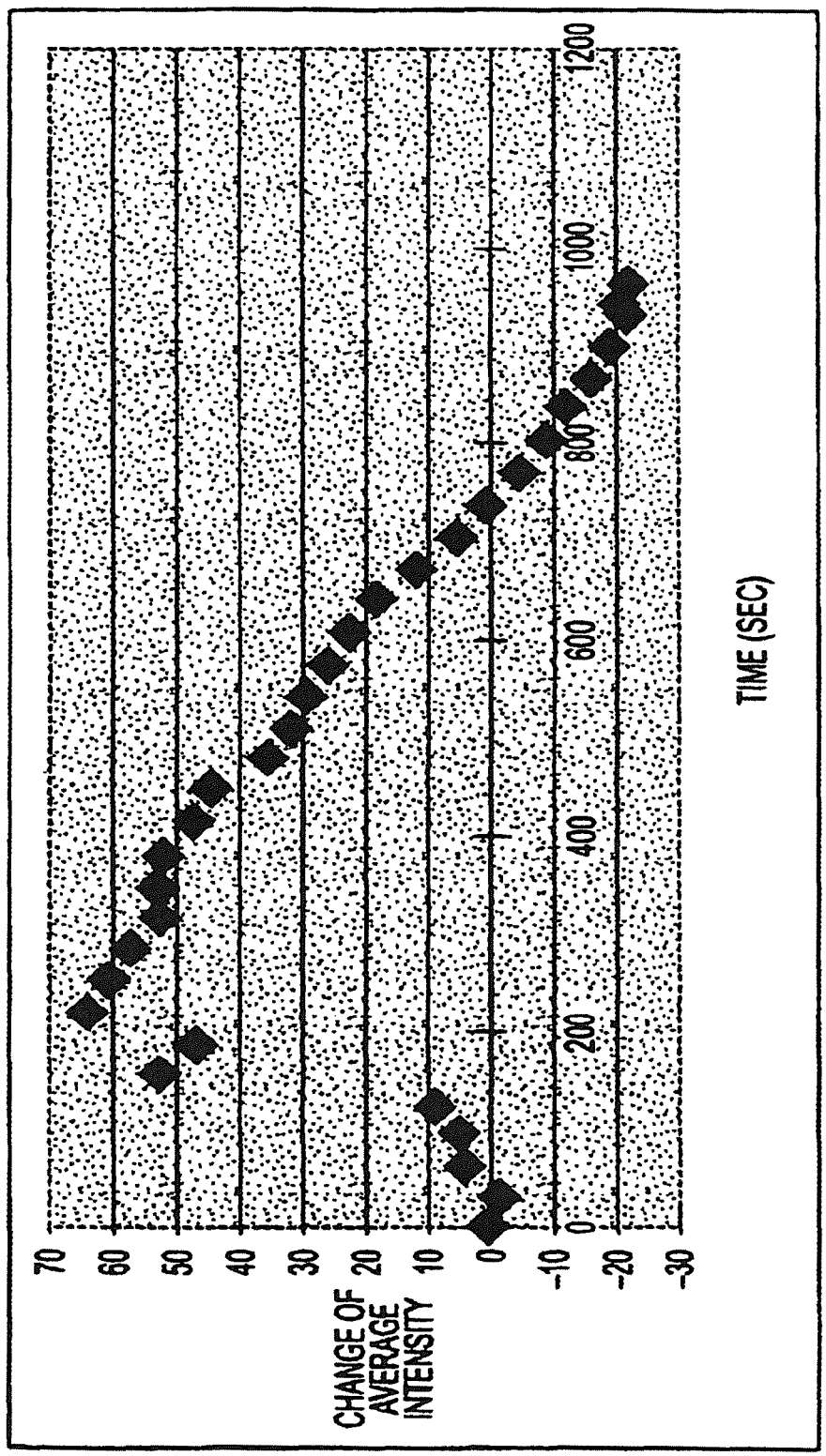
Figure 10C:
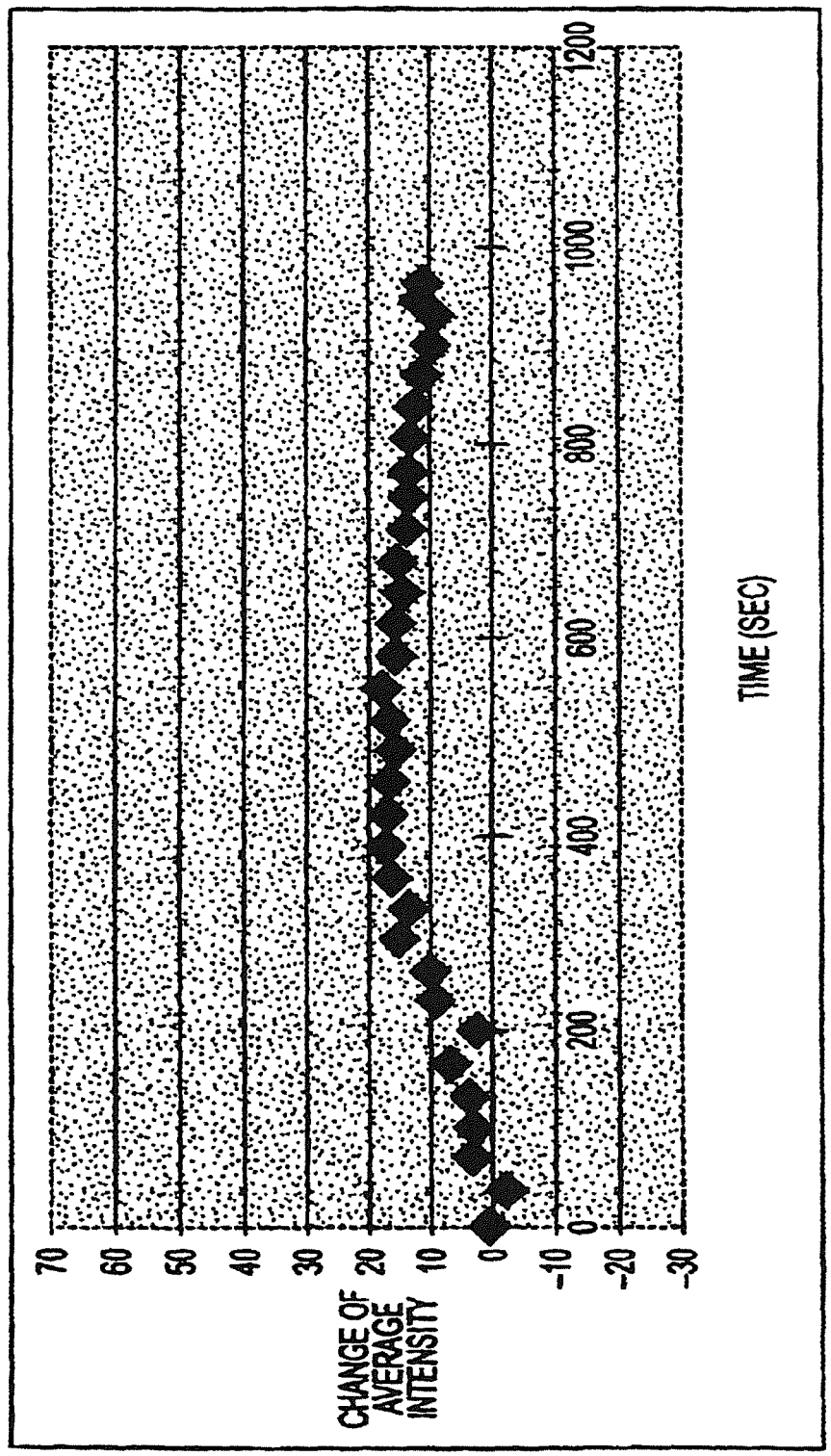
Figure 10D:
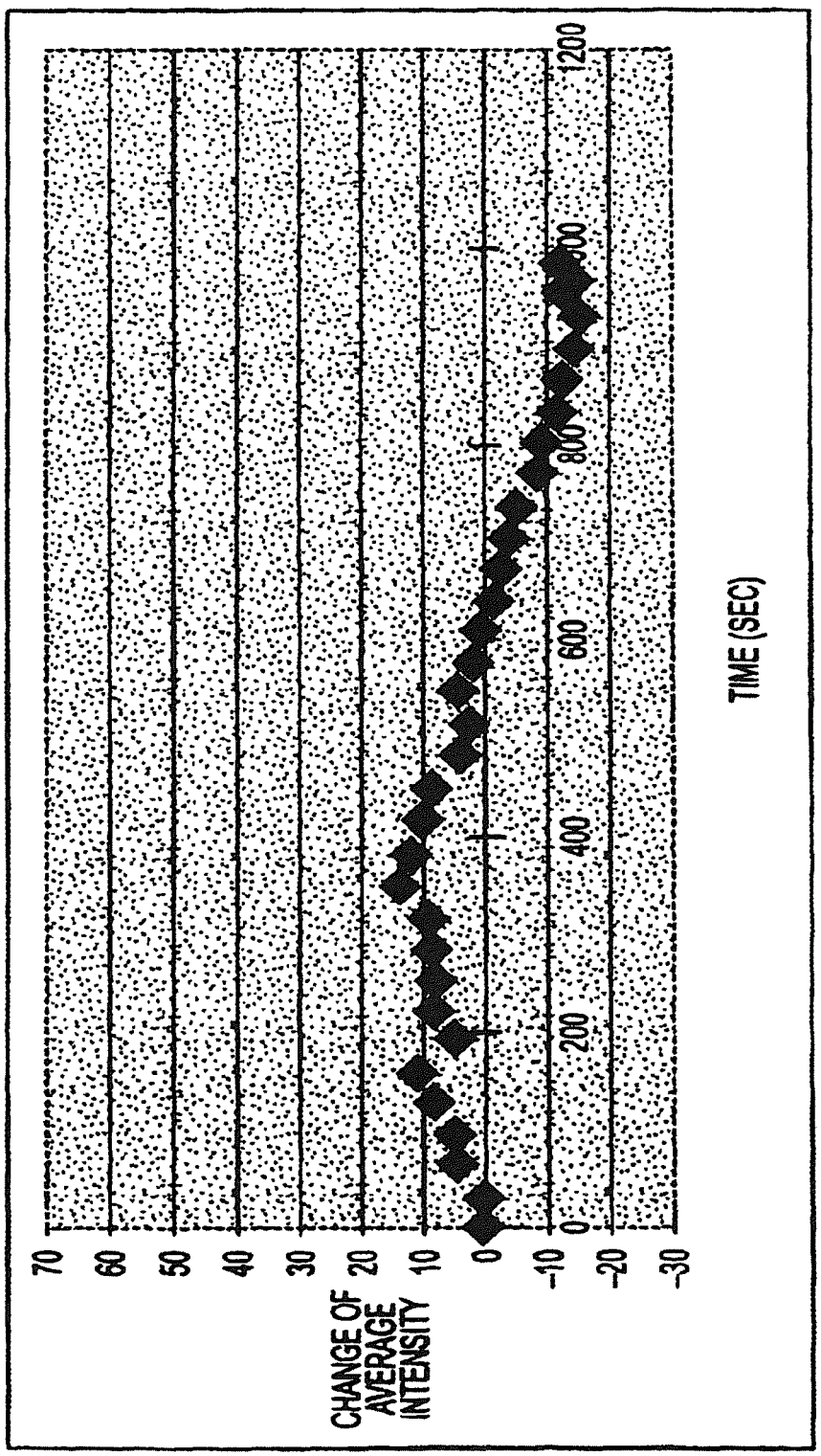
Figure 10E:
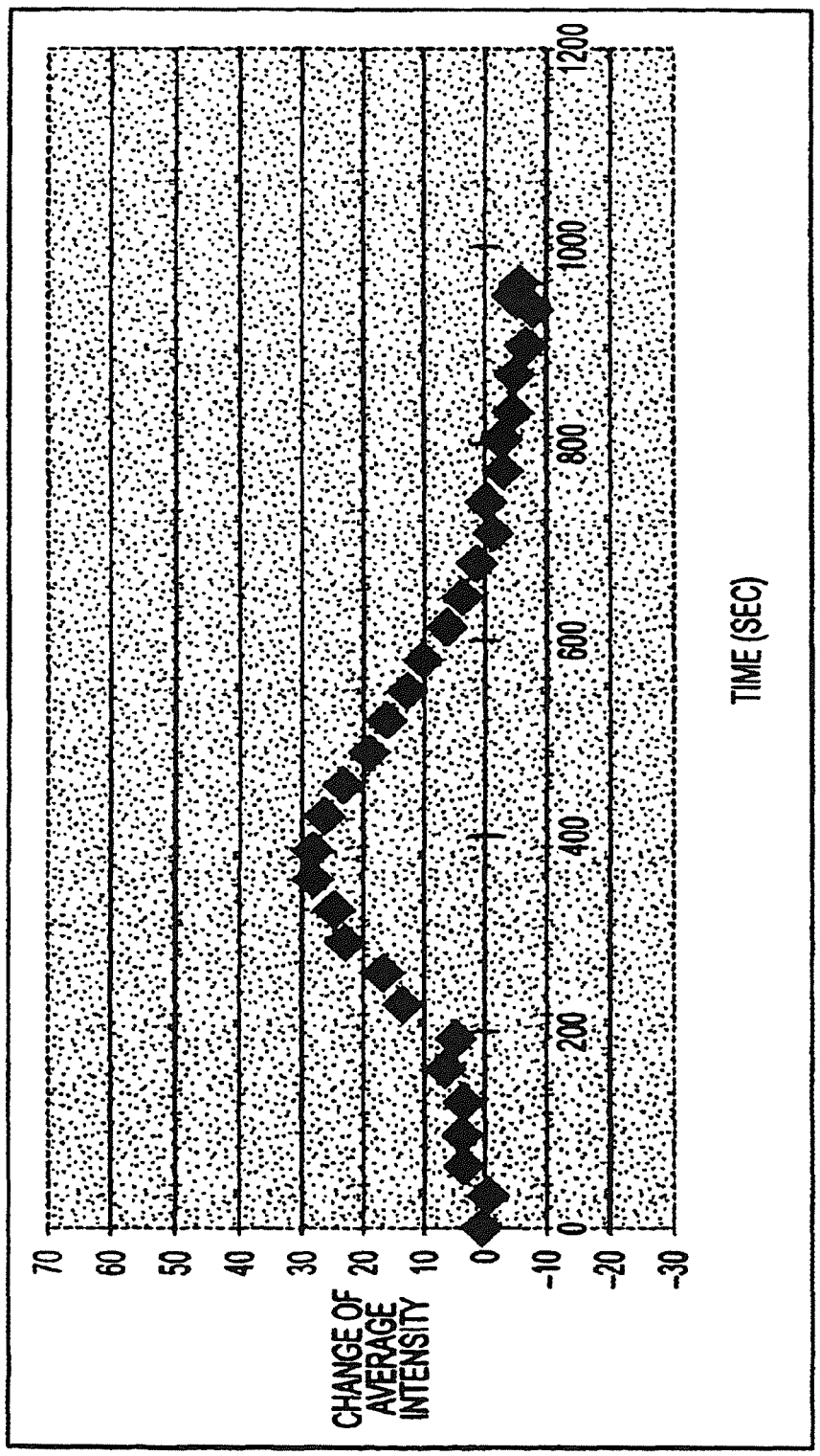
Figure 10F:
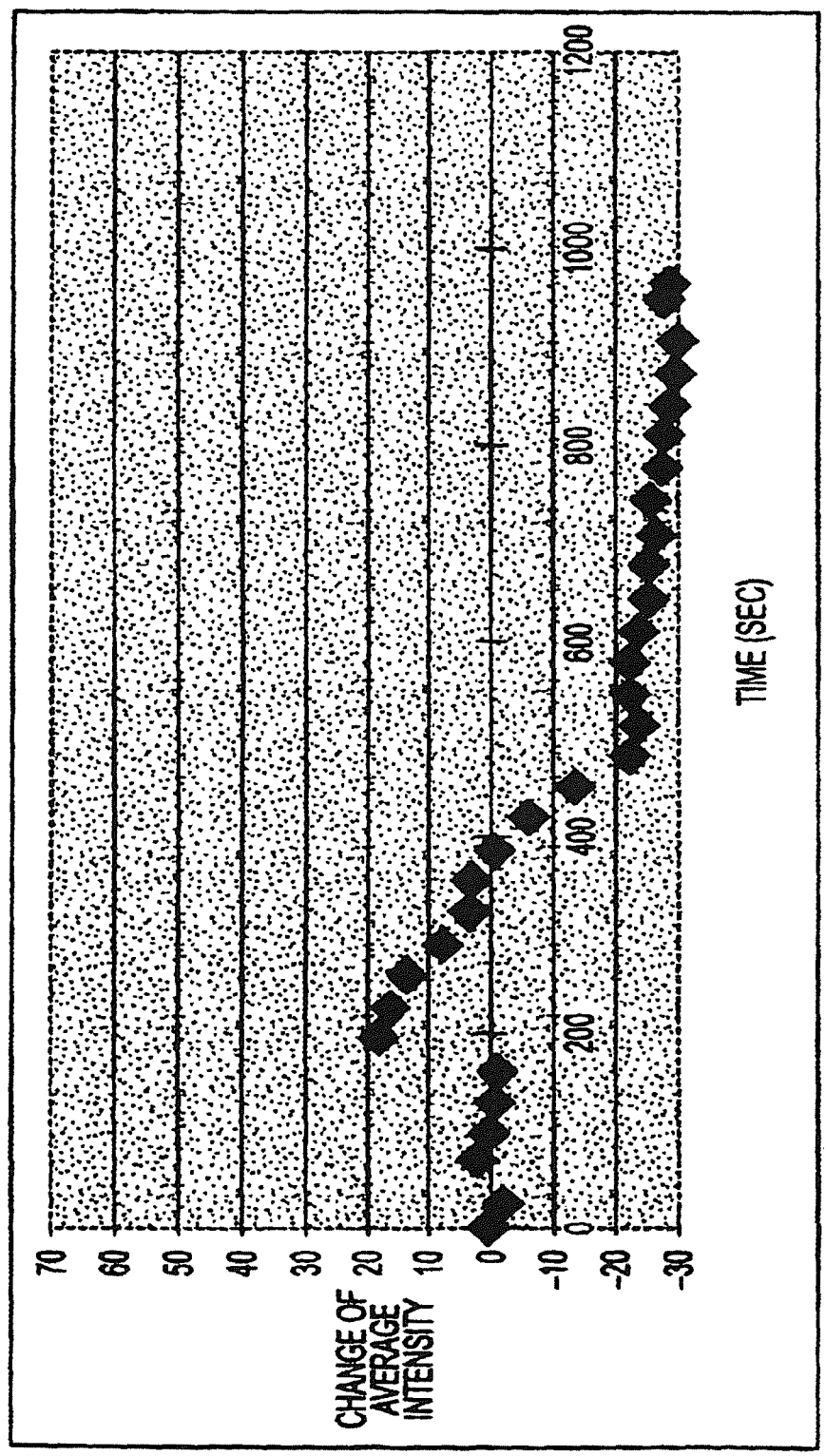
Figure 10G:
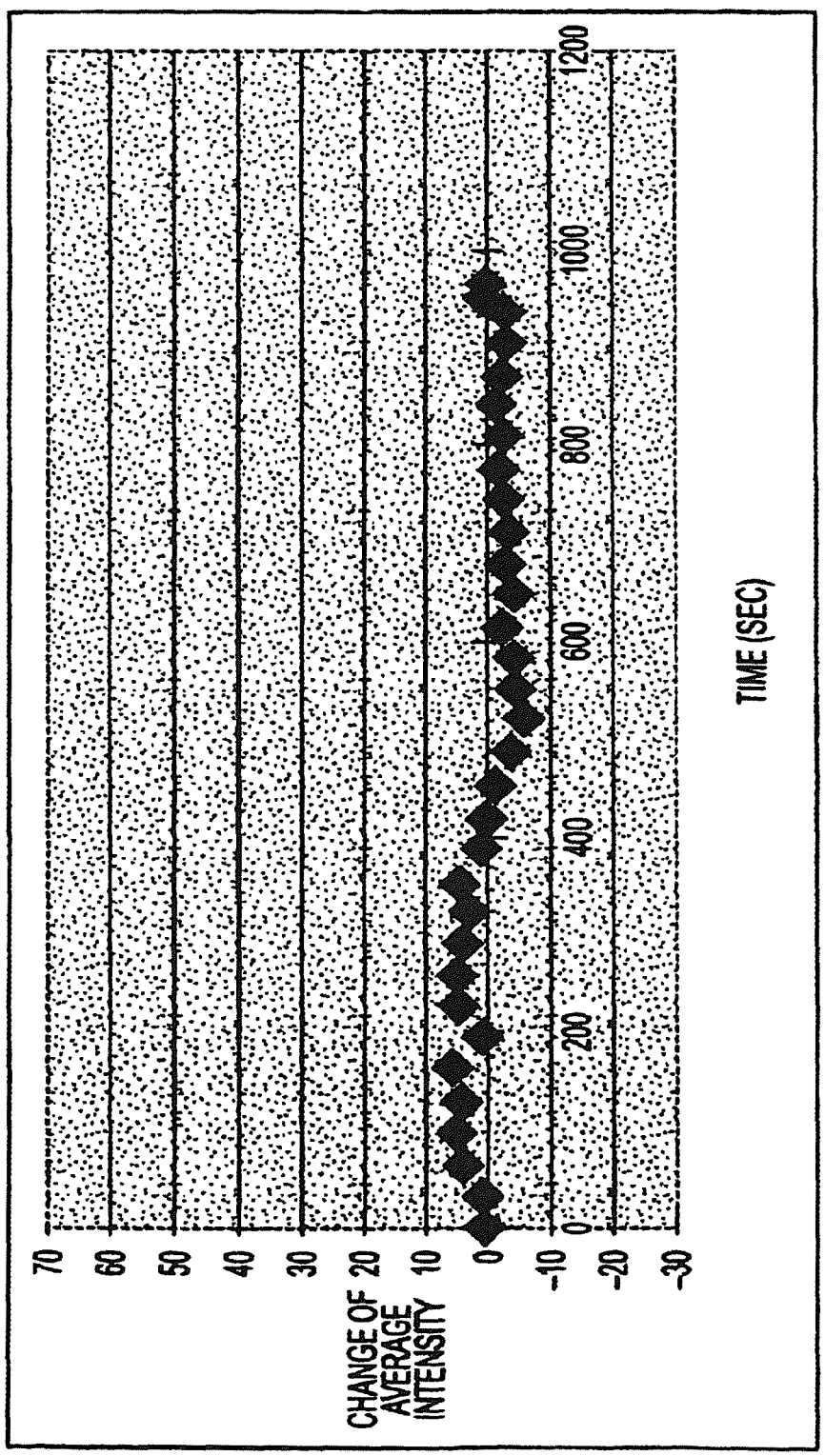
Figure 10H:
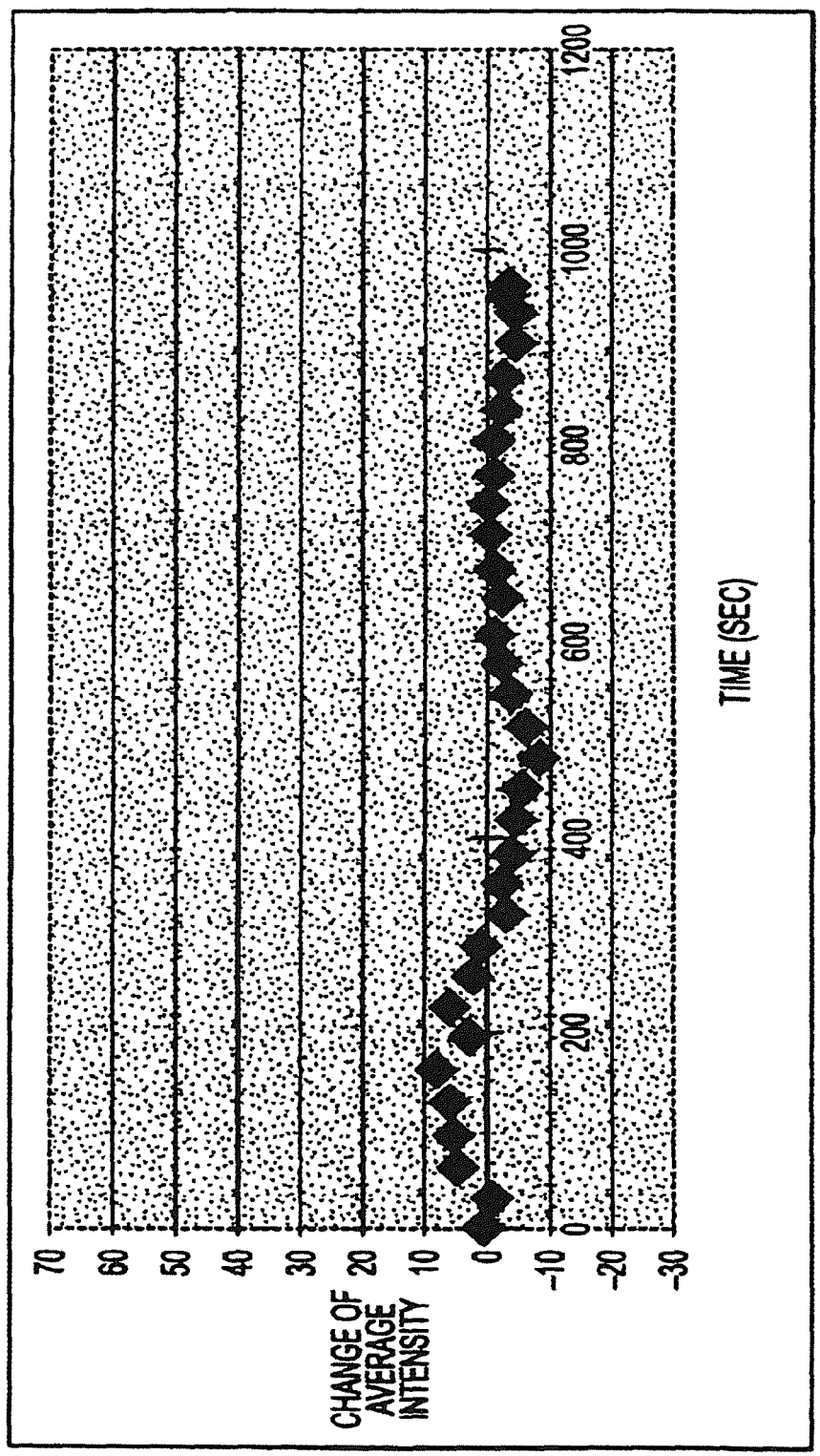

The minimum, maximum, and average pixel value of these images were recorded. The maximum pixel intensities of the center 40×40 mm area of the 50×50 mm whole image was then compared to that of the entire image to avoid potential edge effects (see, FIG. 11). A Turbo C program was written to determine the value and location of the pixel with the maximum intensity.

The final experiment compared the effect of placing an additional 0.5 cm PMMA plate, which will be used in the tissue phantom holder, between the camera and the phantom on the average pixel intensity. Three images (an initial scout and two stereo images) were taken at generator settings of 26 kV, 380 mAs, 100 mA.

Figure 12:
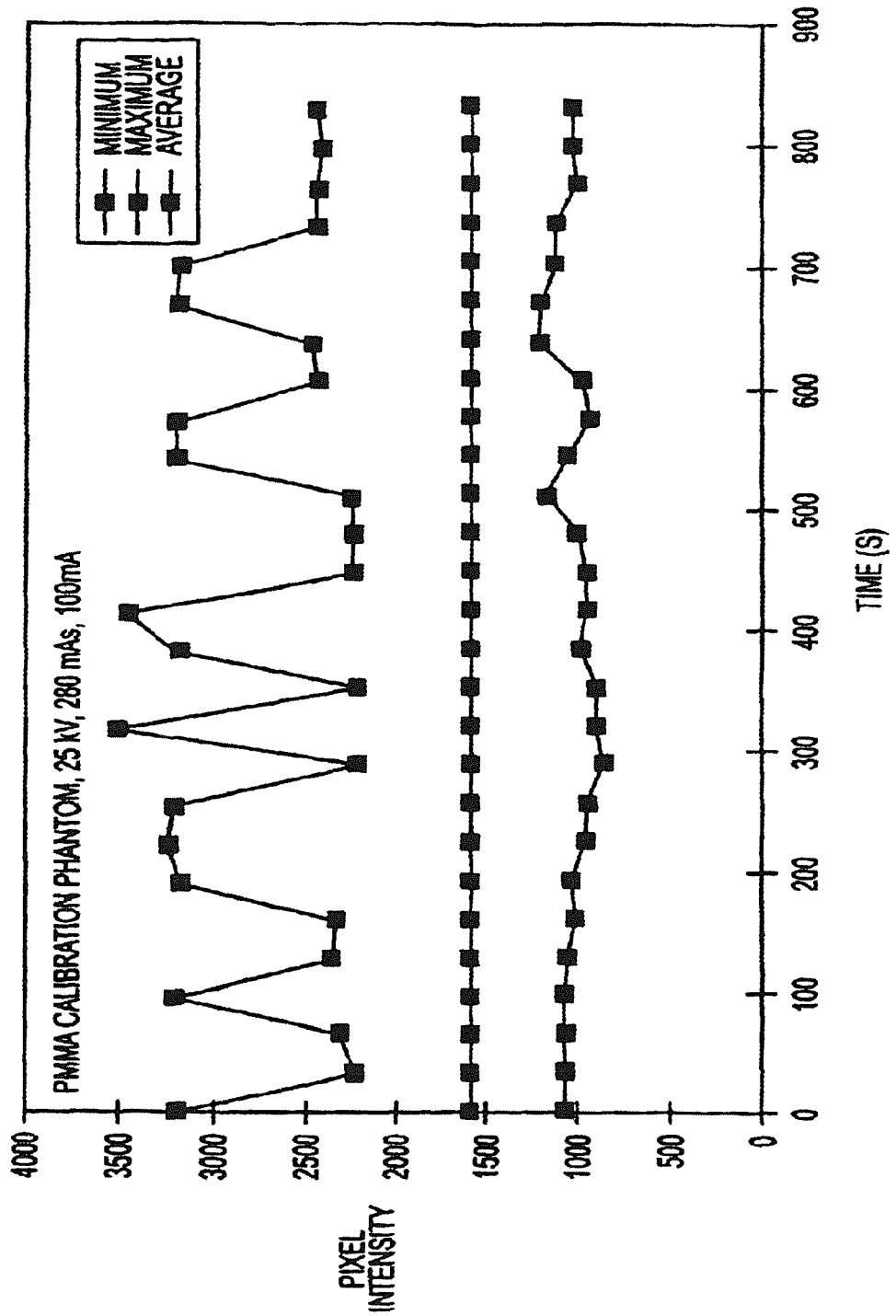
FIG. 12 is a plot of intensity data as a function of time over entire images taken every thirty seconds during an experiment in accordance with the invention.
Figure 13:
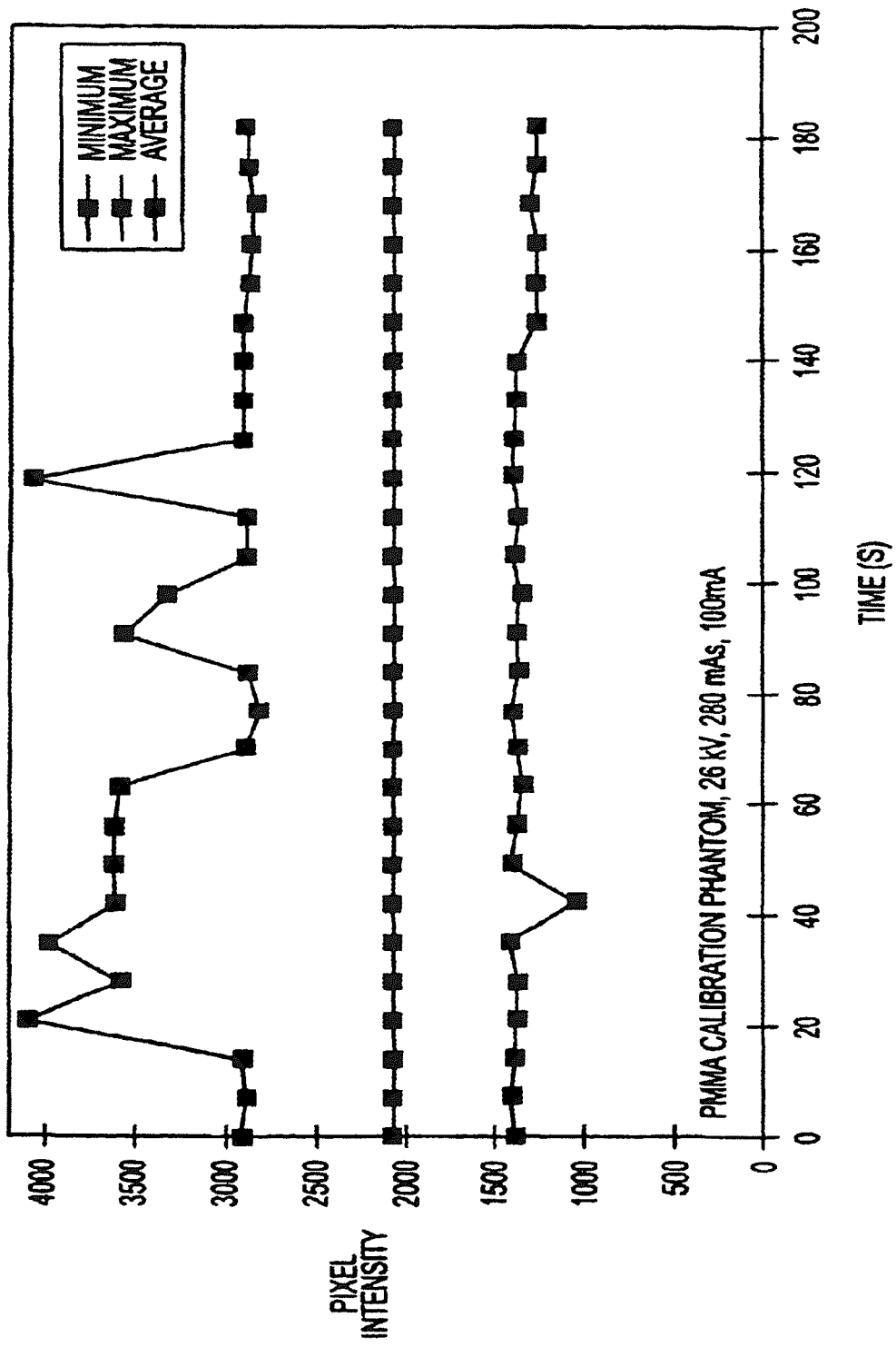
FIG. 13 is a plot of intensity data as a function of time over whole 5 images taken every six seconds in accordance with the invention.
Figure 14:
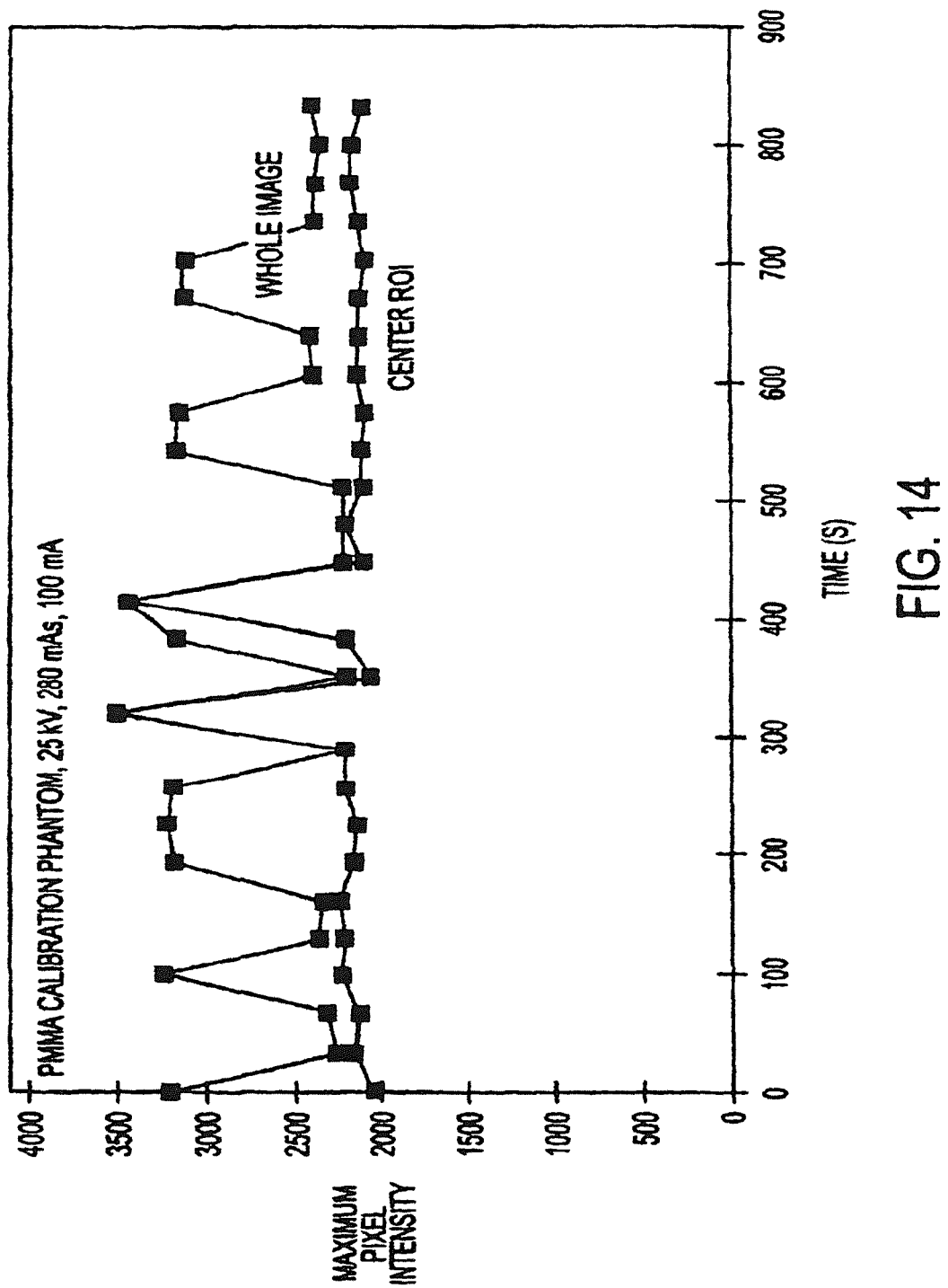
FIG. 14 is a plot of maximum pixel intensities in an experiment in accordance with the invention for thirty second firing sequence of the laser.
Figure 15:
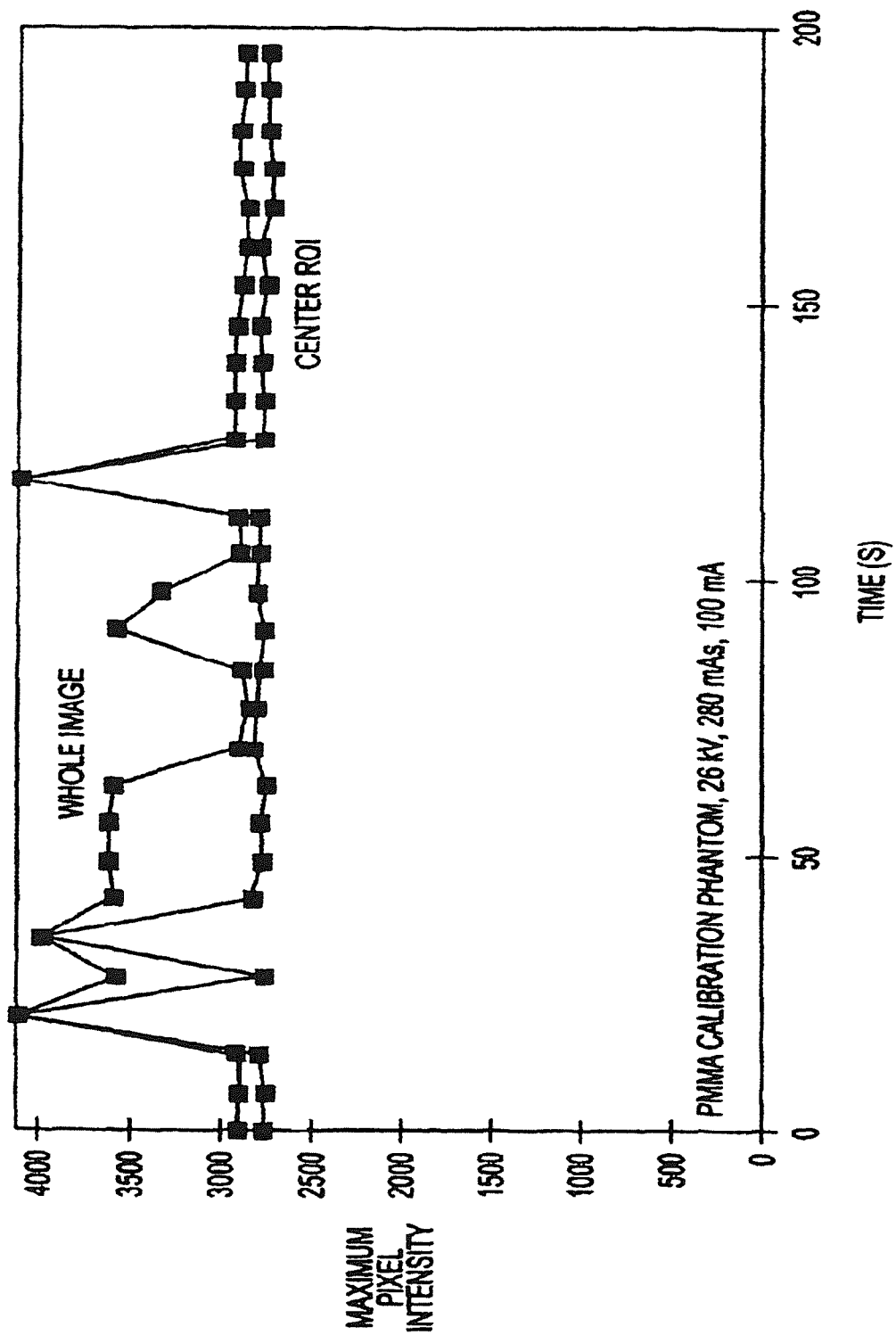
FIG. 15 is a graph of maximum pixel intensities as a function of time in a second experiment for six second firing sequences of the laser.

Results:

The average intensity of the images in the first and second experiments are within 0.5% and 0.2%, respectively (FIGS. 12 and 13). The standard deviations of the average intensities are too small to be visible in FIGS. 12 AND 13. The maximum pixel intensities in both experiments show large variations. Much of these variations disappear when analyzing the center 40×40 mm region, suggesting that the artifact causing these variations occurs more frequently in the edges of the images (see, FIGS. 14 and 15). In the five images where the variations were still apparent in the 40×40 mm region, the variations do not appear in a 30×30 mm center region. The minimum intensity values remained virtually unchanged in the center region (Tables 1-2). According to Tables 3-4, the maximum intensity occurs on the same few pixels throughout the experiment. In both experiments, the maximum intensity value occurs mostly on pixel coordinates (628, 1020, maximum intensity 3170) and (1018, 179, maximum intensity 2400).

The average of the average intensities of the images taken in the last experiment with the additional PMMA plate is 1393, or 66% of the value without the plate, which indicates that the plate introduces a significant attenuation. However, this effect may be compensated for by using other X-ray generator parameters.

Conclusion:

These experiments demonstrate that the pixel intensities of the sequential images are stable, with the exception of a few pixels.

Note:

The minimum pixel intensity is zero and corresponds to total attenuation (i.e., no X-ray photons reaching the camera) and a white image. The maximum pixel intensity is 4095 and corresponds to no attenuation (i.e., all X-ray photons reaching the camera) and a black image. Each pixel corresponds to an area of approximately 50×50 pm.

TABLE 1

Pixel intensity data of Experiment 1 (30 s firing rate, 25 kV, 280 mAs, 100 mA) (RMS [root mean square] represents the standard deviation of the intensity over the whole image)

| | Whole image (50 × 50 mm) | | | | Whole image (40 × 40 mm) | | | |
|---|---|---|---|---|---|---|---|---|
| Time | Minimum | Maximum | Average | RMS | Minimum | Maximum | Average | RMS |
| 0 | 1060 | 3186 | 1588.83 | 19.56 | 1060 | 2024 | 1588.44 | 18.93 |
| 32 | 1060 | 2232 | 1589.25 | 19.65 | 1076 | 2142 | 1588.16 | 18.98 |
| 64 | 1073 | 2297 | 1588.7 | 19.66 | 1073 | 2106 | 1588.18 | 19.01 |
| 96 | 1076 | 3209 | 1588.63 | 19.66 | 1060 | 2219 | 1588.75 | 19.01 |
| 128 | 1052 | 2341 | 1588.51 | 19.8 | 1052 | 2197 | 1587.89 | 19.04 |
| 160 | 1014 | 2318 | 1587.98 | 19.83 | 1014 | 2222 | 1587.37 | 19.06 |
| 192 | 1036 | 3158 | 1587.71 | 19.91 | 1036 | 2139 | 1587.09 | 18.98 |
| 224 | 951 | 3219 | 1587.25 | 19.95 | 951 | 2125 | 1586.55 | 19.02 |
| 256 | 949 | 3192 | 1586.98 | 20.05 | 949 | 2193 | 1586.25 | 19.08 |
| 288 | 859 | 2204 | 1587.07 | 20.01 | 947 | 2204 | 1586.32 | 19.05 |
| 320 | 897 | 3502 | 1586.83 | 20.18 | 934 | 3502 | 1586.03 | 19.27 |
| 352 | 891 | 2194 | 1586.47 | 20.13 | 891 | 2056 | 1585.71 | 19.09 |
| 384 | 971 | 3170 | 1585.91 | 20.24 | 971 | 2204 | 1584.96 | 19.09 |
| 416 | 944 | 3436 | 1585.87 | 20.25 | 944 | 3436 | 1584.96 | 19.15 |
| 448 | 931 | 2216 | 1584.92 | 20.2 | 931 | 2104 | 1583.94 | 19.1 |
| 480 | 985 | 2225 | 1584.96 | 20.27 | 985 | 2207 | 1584.04 | 19.13 |
| 512 | 1151 | 2225 | 1585.21 | 20.26 | 1151 | 2117 | 1584.21 | 19.11 |
| 544 | 1048 | 3179 | 1585.47 | 20.73 | 1048 | 2119 | 1584.44 | 19.13 |
| 576 | 918 | 3162 | 1584.84 | 20.41 | 918 | 2093 | 1583.78 | 19.16 |
| 608 | 951 | 2406 | 1583.94 | 20.36 | 951 | 2146 | 1582.9 | 19.15 |
| 640 | 1191 | 2429 | 1584.76 | 20.41 | 1231 | 2134 | 1583.59 | 19.15 |
| 672 | 1176 | 3151 | 1584.53 | 20.45 | 1227 | 2141 | 1583.36 | 19.1 |
| 704 | 1098 | 3145 | 1584.13 | 20.45 | 1098 | 2102 | 1582.93 | 19.11 |
| 736 | 1088 | 2407 | 1583.24 | 20.4 | 1088 | 2154 | 1582.07 | 19.1 |
| 768 | 975 | 2406 | 1583.32 | 20.49 | 975 | 2203 | 1582.05 | 19.13 |
| 800 | 995 | 2377 | 1581.26 | 20.45 | 995 | 2192 | 1580.01 | 19.11 |
| 832 | 1004 | 2415 | 1580.55 | 20.45 | 1004 | 2128 | 1579.27 | 19.08 |

TABLE 2

Pixel intensity data of Experiment 2 (6 s firing rate, 26 kV, 280 mAs, 100 mA) (RMS [root mean square] represents the standard deviation of the intensity over the whole image)

| Time | Whole image (50 × 50 mm) | | | | | | | |
|---|---|---|---|---|---|---|---|---|
| | Minimum | Maximum | Average | RMS | Minimum | Maximum | Average | RMS |
| | | | | | Whole image (40 × 40 mm) | | | |
| 0 | 1382 | 2901 | 2080.01 | 23.82 | 1382 | 2752 | 2079.76 | 22.47 |
| 7 | 1399 | 2881 | 2080.18 | 23.87 | 1399 | 2751 | 2079.8 | 22.46 |
| 14 | 1388 | 2903 | 2080.72 | 23.97 | 1388 | 2780 | 2080.48 | 22.45 |
| 21 | 1379 | 4095 | 2080.84 | 24.22 | 1379 | 4095 | 2080.53 | 22.78 |
| 28 | 1366 | 3565 | 2080.8 | 24.04 | 1366 | 2743 | 2080.49 | 22.38 |
| 35 | 1413 | 3983 | 2081.27 | 24.38 | 1442 | 3983 | 2081.01 | 0.78 |
| 42 | 1046 | 3588 | 2080.22 | 24.18 | 1444 | 2814 | 2079.87 | 22.44 |
| 49 | 1417 | 3613 | 2080.01 | 24.2 | 1434 | 2764 | 2079.68 | 22.46 |
| 56 | 1379 | 3611 | 2078.74 | 24.26 | 1379 | 2774 | 2078.39 | 22.5 |
| 63 | 1352 | 3584 | 2077.06 | 24.29 | 1352 | 2747 | 2076.59 | 22.47 |
| 70 | 1380 | 2896 | 2076.6 | 24.29 | 1380 | 2806 | 2076.18 | 22.53 |
| 77 | 1415 | 2834 | 2077.31 | 24.32 | 1438 | 2798 | 2076.82 | 22.49 |
| 84 | 1368 | 2879 | 2077.58 | 24.35 | 1368 | 2774 | 2077.09 | 22.47 |
| | | | | | Whole image (50 × 50 mm) | | | |
| 91 | 1390 | 3566 | 2078.24 | 24.49 | 1390 | 2759 | 2077.75 | 22.53 |
| 98 | 1371 | 3330 | 2078.91 | 24.4 | 1371 | 2800 | 2078.4 | 22.49 |
| 105 | 1405 | 2893 | 2078.73 | 24.48 | 1405 | 2790 | 2078.15 | 22.53 |
| 112 | 1382 | 2895 | 2079.08 | 24.53 | 1382 | 2784 | 2078.54 | 22.54 |
| 119 | 1419 | 4095 | 2078.55 | 24.85 | 1444 | 4095 | 2077.98 | 23.11 |
| 126 | 1407 | 2919 | 2079.31 | 24.6 | 1441 | 2755 | 2078.69 | 22.57 |
| 133 | 1392 | 2915 | 2078.88 | 24.63 | 1390 | 2772 | 2078.28 | 22.52 |
| 140 | 1401 | 2917 | 2078.76 | 24.68 | 1401 | 2779 | 2078.13 | 22.61 |
| 147 | 1282 | 2913 | 2079.35 | 24.64 | 1282 | 2802 | 2078.74 | 22.54 |
| 154 | 1297 | 2879 | 2079.54 | 24.73 | 1291 | 2745 | 2078.91 | 22.63 |
| 161 | 1285 | 2872 | 2079.84 | 24.77 | 1285 | 2787 | 2079.16 | 22.62 |
| 168 | 1314 | 2855 | 2079.93 | 24.77 | 1314 | 2729 | 2079.24 | 22.62 |
| 175 | 1288 | 2898 | 2079.87 | 24.8 | 1288 | 2723 | 2079.19 | 22.71 |
| 182 | 1297 | 2903 | 2079.39 | 24.8 | 1297 | 2744 | 2078.68 | 22.58 |
| 189 | 1271 | 2880 | 2078.14 | 24.83 | 1271 | 2744 | 2077.43 | 22.65 |
| 196 | 1262 | 2866 | 2078.02 | 24.86 | 1262 | 2746 | 2077.29 | 22.6 |

TABLE 3

Values and pixel coordinates of maximum intensities

| Experiment 1 | | | | Experiment 2 | | | |
|---|---|---|---|---|---|---|---|
| Time | Minimum | X-coordinate | Y-coordinate | Time | Minimum | X-coordinate | Y-coordinate |
| 0 | 3186 | 628 | 1020 | 0 | 2901 | 1018 | 179 |
| 32 | 3209 | 628 | 1020 | 7 | 2881 | 1018 | 179 |
| 64 | 2297 | 966 | 681 | 14 | 2903 | 1018 | 179 |
| 96 | 2232 | 970 | 63 | 21 | 4095 | 834 | 798 |
| 128 | 2341 | 966 | 681 | 28 | 3565 | 628 | 1020 |
| 160 | 2318 | 977 | 754 | 35 | 3983 | 634 | 341 |
| 192 | 3158 | 628 | 1020 | 42 | 3588 | 628 | 1020 |
| 224 | 3219 | 628 | 1020 | 49 | 3613 | 628 | 1020 |
| 256 | 3192 | 628 | 1020 | 56 | 3611 | 628 | 1020 |
| 288 | 2204 | 162 | 534 | 63 | 3584 | 628 | 1020 |
| 320 | 3502 | 669 | 304 | 70 | 2896 | 1018 | 179 |
| 352 | 2194 | 977 | 754 | 77 | 2834 | 1018 | 179 |
| 384 | 3170 | 628 | 1020 | 84 | 2879 | 1018 | 179 |
| 416 | 3436 | 396 | 195 | 91 | 3566 | 628 | 1020 |
| 448 | 2216 | 977 | 754 | 98 | 3330 | 628 | 1020 |
| 480 | 2225 | 977 | 754 | 105 | 2893 | 1018 | 179 |
| 512 | 2225 | 970 | 63 | 112 | 2895 | 1018 | 179 |
| 544 | 3179 | 628 | 1020 | 119 | 4095 | 912 | 171 |
| 576 | 3162 | 628 | 1020 | 126 | 2919 | 1018 | 179 |
| 608 | 2406 | 1018 | 179 | 133 | 2915 | 1018 | 179 |
| 640 | 2429 | 1018 | 179 | 140 | 2917 | 1018 | 179 |
| 672 | 3151 | 628 | 1020 | 147 | 2913 | 1018 | 179 |
| 704 | 3145 | 628 | 1020 | 154 | 2879 | 1018 | 179 |
| 736 | 2407 | 1018 | 179 | 161 | 2872 | 964 | 65 |
| 768 | 2406 | 1018 | 179 | 168 | 2855 | 1018 | 179 |
| 800 | 2377 | 1018 | 179 | 175 | 2898 | 1018 | 179 |

TABLE 3-continued

Values and pixel coordinates of maximum intensities

| Experiment 1 | | | | Experiment 2 | | | |
|---|---|---|---|---|---|---|---|
| Time | Minimum | X-coordinate | Y-coordinate | Time | Minimum | X-coordinate | Y-coordinate |
| 832 | 2415 | 1018 | 179 | 182 | 2903 | 1018 | 179 |
| | | | | 189 | 2880 | 1018 | 179 |
| | | | | 196 | 2866 | 1018 | 179 |

Analysis of Thermally-Induced Changes in Mammovision Images by Pixel Averaging

This subsection describes test results that display changes in sequential images taken with the MAMMOVISION System on the PMMA calibration phantom and on laser-irradiated fatty porcine tissue.

The images taken with the MAMMOVISION system are 50×50 mm images containing 1024×1024 pixels with each pixel corresponding to a 50×50 p.m area. Since the desired target volume is 30 mm in diameter, the main region of interest (ROI) during treatment is a 30×30 mm area in the image. These data in ASCII (text) files containing the intensity for each pixel are 5 MB each. These files are too large to handle when dealing with multiple images. In addition, the resolution of the images is much greater for each image than is necessary for thermal imaging; where a resolution on the order of 1×1 mm is sufficient. It is therefore beneficial to convert the images from 1024×1024 pixels to a smaller resolution by averaging blocks of the 1024×1024 into one pixel (see, Table 4). Another benefit of reducing the resolution is removing the noise effects generated by a few unstable pixels.

TABLE 4

Number of pixels and resolution of averaged images

| Number of Pixels | Size Averaged Block | Pixel Size of Average Images | Number of Pixels in 30 × 30 mm ROI |
|---|---|---|---|
| 1024 × 1024 (no averaging) | 1 × 1 | 50 × 50 μm | 600 × 600 |
| 512 × 512 | 2 × 2 | 0.1 × 0.1 mm | 300 × 300 |
| 256 × 256 | 4 × 4 | 0.2 × 0.2 mm | 150 × 150 |
| 128 × 128 | 8 × 8 | 0.4 × 0.4 mm | 75 × 75 |
| 64 × 64 | 16 × 16 | 0.8 × 0.8 mm | 37 × 37 |

Stability of 1024×1024 Images:

In a previous experiment (see, above), the average pixel intensity of the entire 1024×1024 image of the PMMA calibration phantom is shown to be stable within 0.5% in the sequential-firing mode. The purpose of this study was to quantify the stability of each pixel.

The Experimental Method:

The PMMA calibration block (10×10×4 cm) was held in place before the MAMMOVISION (85200G-2, Fischer Imaging Co., Denver, Colo.) camera with the compression paddle at room temperature (25° C.). The initial scout was taken at 00 in the Autoexposure mode and its parameters were used in the subsequent firing. The generator was set manually at 25 kV, 280 mAs, and 100 mA for the sequential firing. The auto-firing sequence was set to take exposures every 30 seconds for approximately 14 minutes for a total of 27 images. A Turbo C program was written to find pixels that changed in intensity by more than 20% between two successive images.

Results:

The analysis of the 27 1024×1024 images revealed that only 90 pixels 15 showed significant variation (>20%) at least once during the experiment (Table 5). The maximum number of pixels that changed by more than 20% from one image to the next was 19. This analysis corroborates the earlier findings that the pixel intensities of the sequential images are stable, with the exception of a small percentage of pixels.

TABLE 5

Coordinates of pixels with intensity change greater than 20%

| X-coordinate | Y-coordinate | Number Of Occurrences | Maximum Percent Change |
|---|---|---|---|
| 15 | 538 | 3 | 23.2 |
| 157 | 110 | 2 | 22.6 |
| 162 | 534 | 10 | 38.8 |
| 181 | 473 | 4 | 44.5 |
| 208 | 521 | 10 | 30.1 |
| 212 | 584 | 14 | 32.6 |
| 227 | 23 | 3 | 25.1 |
| 234 | 992 | 1 | −30.4 |
| 253 | 516 | 1 | 20.4 |
| 302 | 275 | 6 | −39.6 |
| 305 | 652 | 4 | 23.1 |
| 312 | 601 | 7 | 52.3 |
| 327 | 474 | 6 | 40.9 |
| 329 | 1004 | 6 | 34.6 |
| 340 | 768 | 3 | 50.0 |
| 344 | 408 | 1 | 24.6 |
| 389 | 885 | 3 | 75.5 |
| 395 | 4 | 7 | 36.2 |
| 396 | 195 | 2 | 115.6 |
| 421 | 882 | 1 | 22.8 |
| 457 | 899 | 5 | 28.9 |
| 459 | 906 | 3 | 38.3 |
| 472 | 488 | 4 | 33.6 |
| 476 | 324 | 1 | −20.8 |
| 484 | 304 | 2 | 24.2 |
| 484 | 584 | 1 | 20.4 |
| 493 | 178 | 1 | 25.8 |
| 494 | 770 | 4 | 66.6 |
| 528 | 113 | 1 | −21.7 |
| 536 | 853 | 4 | 61.4 |
| 571 | 217 | 2 | 56.2 |
| 572 | 1001 | 2 | 22.5 |
| 603 | 162 | 2 | 31.0 |
| 614 | 906 | 6 | 32.4 |
| 624 | 153 | 1 | 20.2 |
| 628 | 1020 | 10 | 99.6 |
| 635 | 724 | 1 | 23.8 |
| 653 | 66 | 4 | 25.5 |
| 660 | 978 | 4 | 35.3 |
| 669 | 303 | 2 | 34.4 |
| 669 | 304 | 2 | 123.3 |
| 669 | 388 | 2 | 22.3 |
| 670 | 304 | 2 | 62.2 |
| 674 | 388 | 1 | 23.7 |
| 682 | 0 | 4 | 83.9 |
| 686 | 947 | 2 | 22.9 |
| 711 | 1011 | 4 | 131.5 |
| 716 | 12 | 1 | 23.4 |
| 731 | 805 | 2 | 34.4 |
| 743 | 241 | 2 | 22.2 |

TABLE 5-continued

Coordinates of pixels with intensity change greater than 20%

| X-coordinate | Y-coordinate | Number Of Occurrences | Maximum Percent Change |
|---|---|---|---|
| 745 | 646 | 8 | 46.5 |
| 749 | 358 | 5 | 40.0 |
| 774 | 970 | 2 | 23.1 |
| 778 | 703 | 2 | 22.2 |
| 789 | 938 | 6 | 27.3 |
| 808 | 527 | 1 | 44.2 |
| 809 | 415 | 3 | 22.8 |
| 825 | 586 | 2 | 24.9 |
| 830 | 238 | 1 | 20.2 |
| 847 | 127 | 1 | 21.3 |
| 854 | 630 | 8 | 44.8 |
| 892 | 604 | 4 | 32.2 |
| 903 | 670 | 1 | 20.7 |
| 903 | 832 | 4 | 26.7 |
| 909 | 714 | 1 | 21.5 |
| 912 | 208 | 1 | 20.5 |
| 924 | 663 | 8 | 92.5 |
| 926 | 164 | 5 | 48.4 |
| 928 | 468 | 3 | 22.7 |
| 929 | 983 | 7 | 75.4 |
| 932 | 474 | 6 | 38.5 |
| 935 | 986 | 3 | 28.3 |
| 942 | 262 | 3 | 28.8 |
| 947 | 400 | 2 | 20.8 |
| 964 | 65 | 6 | 59.7 |
| 966 | 681 | 1 | 20.1 |
| 970 | 63 | 5 | 89.5 |
| 976 | 958 | 3 | 26.9 |
| 978 | 25 | 1 | 20.7 |
| 979 | 161 | 1 | 27.9 |
| 981 | 234 | 1 | 27.2 |
| 986 | 281 | 1 | 24.7 |
| 987 | 878 | 2 | 21.3 |
| 994 | 221 | 8 | 42.1 |
| 995 | 53 | 2 | −28.6 |
| 997 | 91 | 3 | 23.2 |
| 100 | 791 | 1 | 24.5 |
| 1003 | 809 | 7 | 36.5 |
| 1014 | 669 | 4 | 25.6 |
| 1017 | 280 | 1 | 27.7 |
| 1018 | 179 | 2 | 56.1 |
| 1022 | 898 | 13 | 31.0 |

Table 5: Coordinates of pixels with intensity change greater than 20%

Stability of 128×128 Images

This subsection describes results of quantifying the stability of the 5 pixel intensities of 128×128 averaged images.

The Experimental Method:

The images used in the previous analysis were converted from 1024×1024 pixel images into 128×128 pixel images by averaging 8×8 pixel blocks into one pixel, by using a Turbo C program. These images were then analyzed 10 by another Turbo C program to find pixels that changed in intensity by more than 2%.

Results:

In the 27 128×128 pixel images, only 8 pixels showed variation of greater than 2% (see, Table 6). The maximum variation was 3.3%, which was 15 in a pixel that increased by that percentage in one image and then decreased to approximately its original value in the next image. No other pixel showed more than a 2% change more than once. The maximum number of pixels changing by more than 2% between two consecutive images was 2. These results indicate that any image changes of more than 5% in 128×128 images 20 will be significant (above noise level) during laser-irradiation.

TABLE 6

Coordinates and image number of pixels with over 2% intensity change in the 128 × 128 images

| X-coordinate | Y-coordinate | Image Number | Percent change |
|---|---|---|---|
| 6 | 73 | 4 | −2.04 |
| 10 | 59 | 15 | −2.07 |
| 35 | 96 | 20 | 2.13 |
| 49 | 24 | 15 | 2.16 |
| 78 | 127 | 24 | 2.15 |
| 83 | 38 | 11 | −3.12 |
| 83 | 38 | 12 | 3.44 |
| 92 | 5 | 3 | 2.17 |
| 120 | 73 | 17 | 2.03 |

Colorized Display of Changes in Laser-Irradiated Tissue:

This subsection describes displaying the changes in X-ray intensity of laser-irradiated tissue in color according to this invention.

The Analytical Method:

The images of the laser-irradiated fatty porcine tissue were obtained from a previous experiment. A 20×8×3 cm piece of fatty porcine tissue with the skin was compressed at room temperature of 25° C. with the MAMMOVISION compression paddle. An optical fiber (REM Series B) with a diffusing tip of diameter 1.7 mm was inserted in the tissue after making a path with a stainless steel trocar (2.1 mm diameter). The laser was fired for 6 minutes at 10 W after the first image was taken and turned off for the remainder of the experiment.

After the initial stereo images were taken to ensure that the fiber was 5 within view of the camera, we began the autofiring sequence. The sequence was set to take images ever 30 seconds for the first 30 exposures, although the system actually took exposures every 32 seconds.

These images were then converted to 128×128 pixel images and each image was subtracted from the first image. These images were then colorized using MICROCAL ORIGIN to show changes around the fiber with time. Two color scales are compared: linear and logarithmic.

Results:

In FIGS. 17A-21B, the changes in the tissue surrounding the fiber are evident. The changes are more apparent in the logarithmic scale than in the linear scale. Movement of the fiber during the experiment cause the red and white regions at the original location of the fiber and the dark blue region at the actual location of the fiber.

Conclusion

From the stability analysis of the 128×128 pixel images of the calibration phantom, it can be assumed that intensity changes above 5% are assumed to be due either to thermal expansion or to tissue movement. These changes show that X-ray images can be utilized to monitor tissue changes during laser irradiation in accordance with this invention.

Figure 16A:
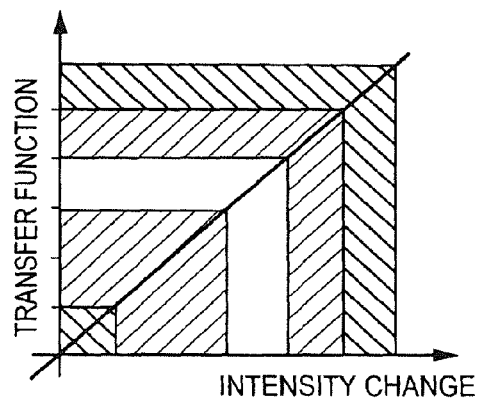
FIG. 16A illustrates transfer function as a function of intensity on a linear scale.
Figure 16B:
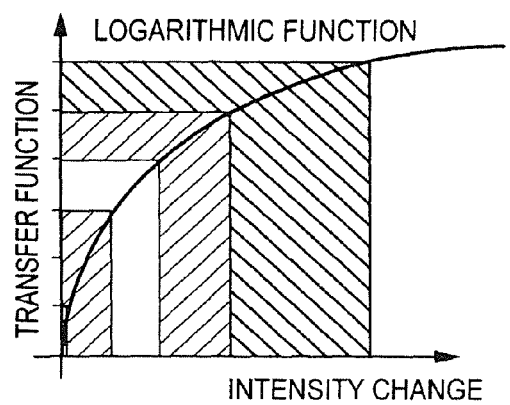
FIG. 16B illustrates a transfer function vs. intensity change on a logarithmic scale.
Figure 16C:
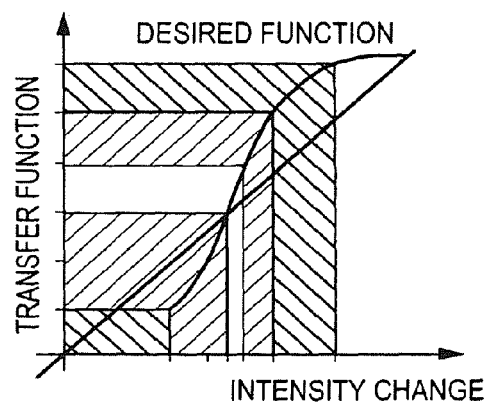
FIG. 16C illustrates a transfer function vs. intensity change for a 15 desired function.
Figure 17A:
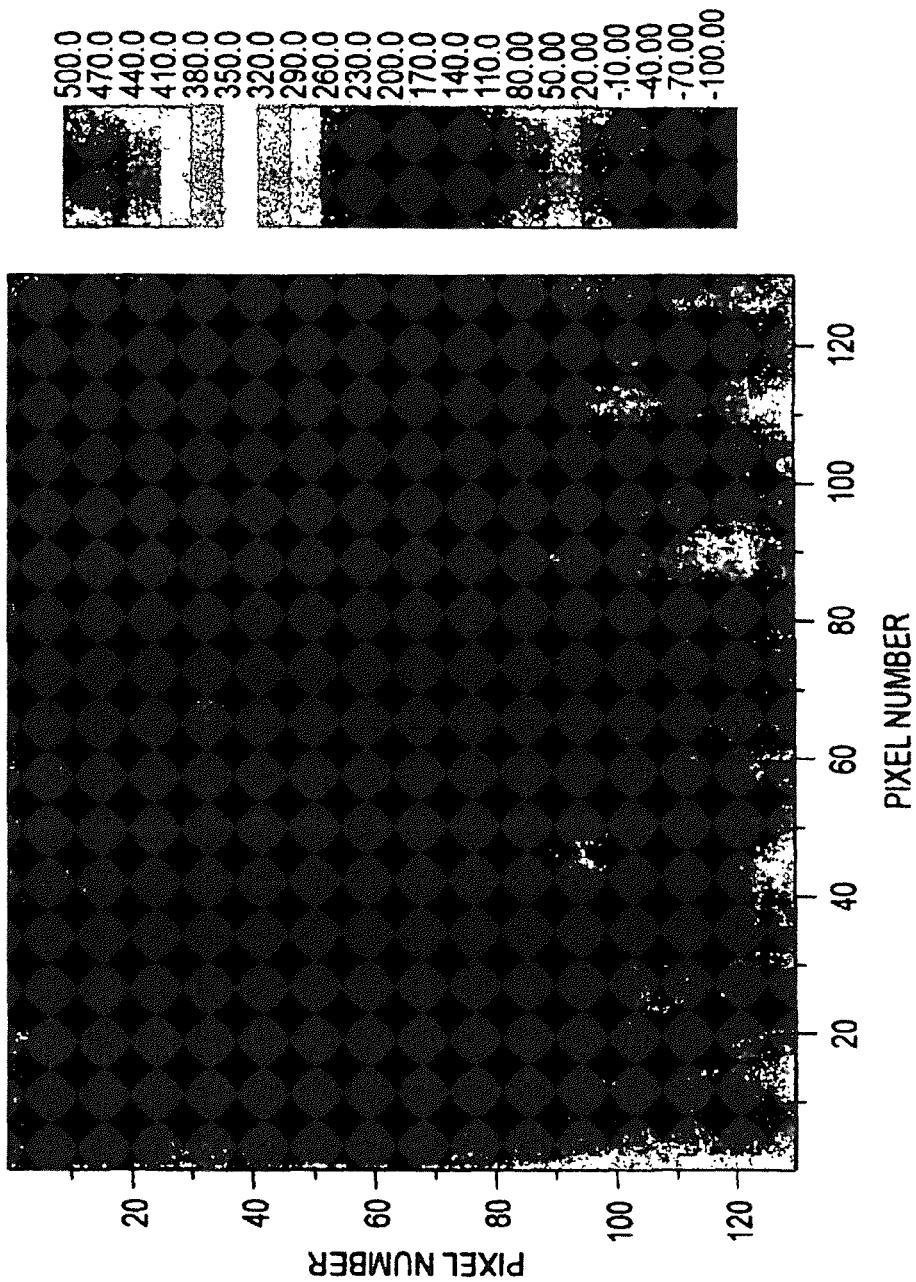
FIG. 17A is an initial subtracted image on a linear scale for data taking in accordance with a preferred embodiment of this invention.
Figure 17B:
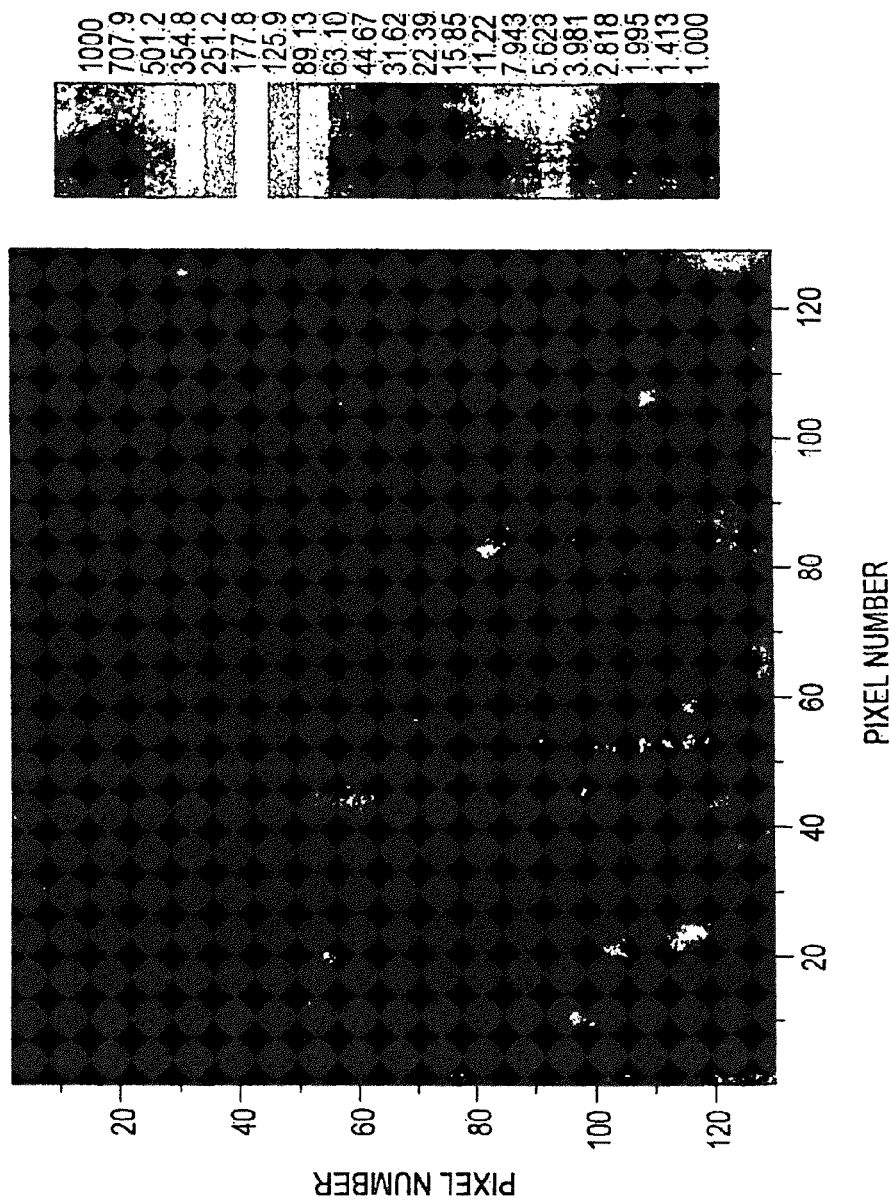
FIG. 17B is an initial subtracted image on a logarithmic scale for data taken in accordance with a preferred embodiment of this invention.
Figure 18A:
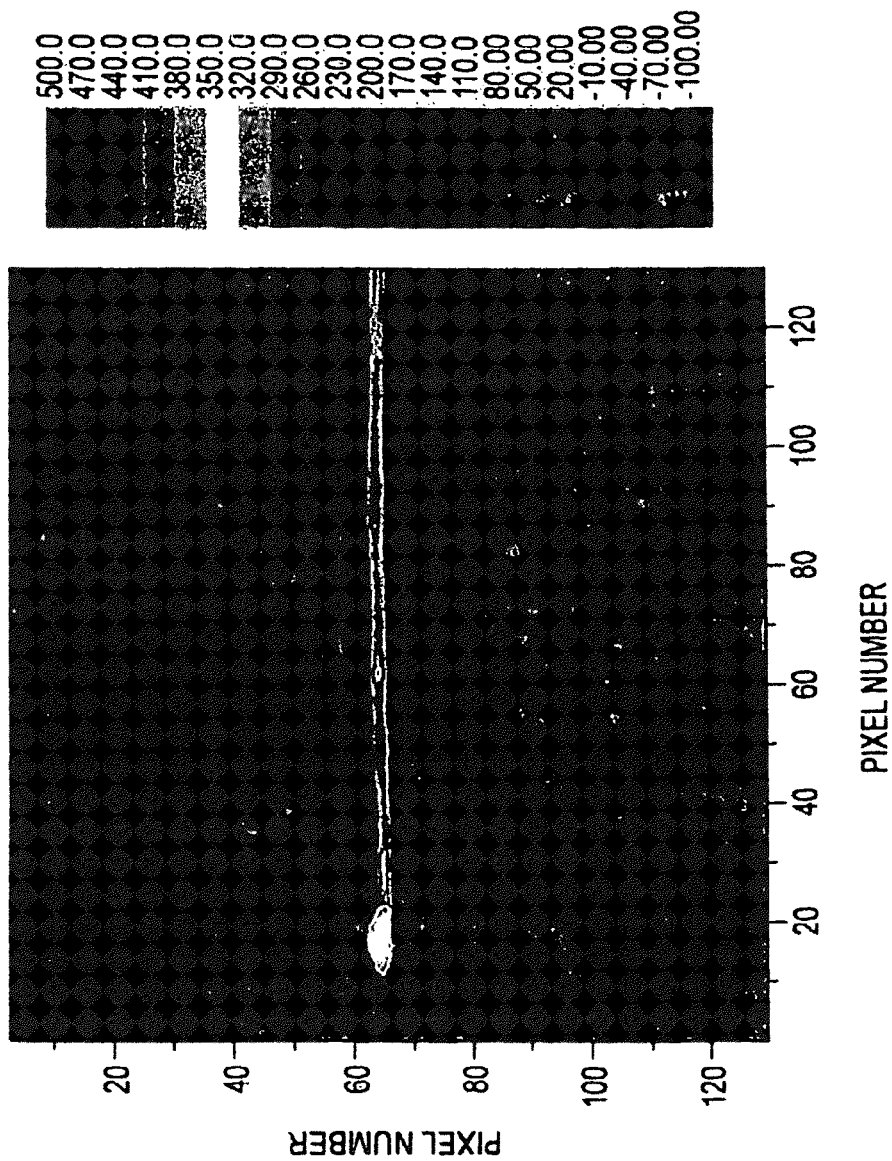
FIG. 18A is a subtracted image after 3 minutes of laser firing on the linear scale for data taken in accordance with a preferred embodiment of this invention (difference image)
Figure 18B:
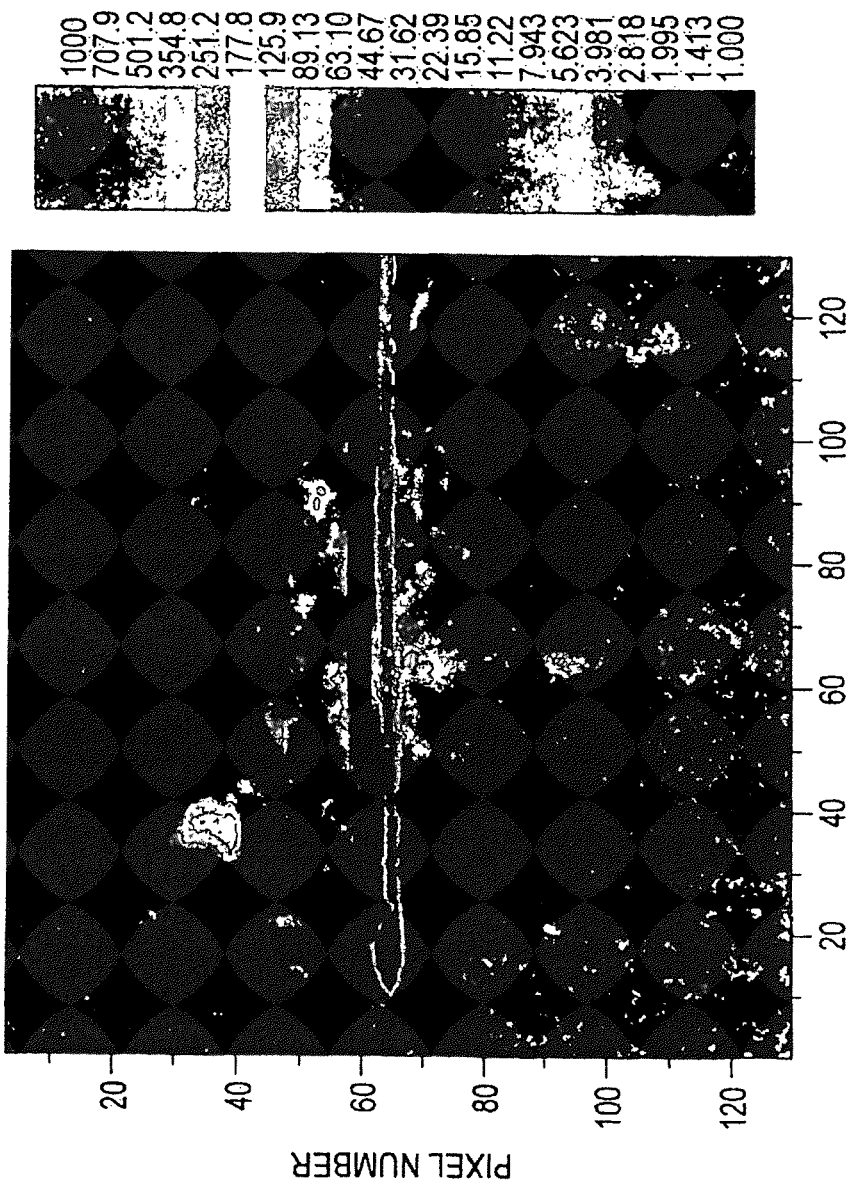
FIG. 18B is a subtracted image on a logarithmic scale corresponding to the case of FIG. 18A (difference image)
Figure 19A:
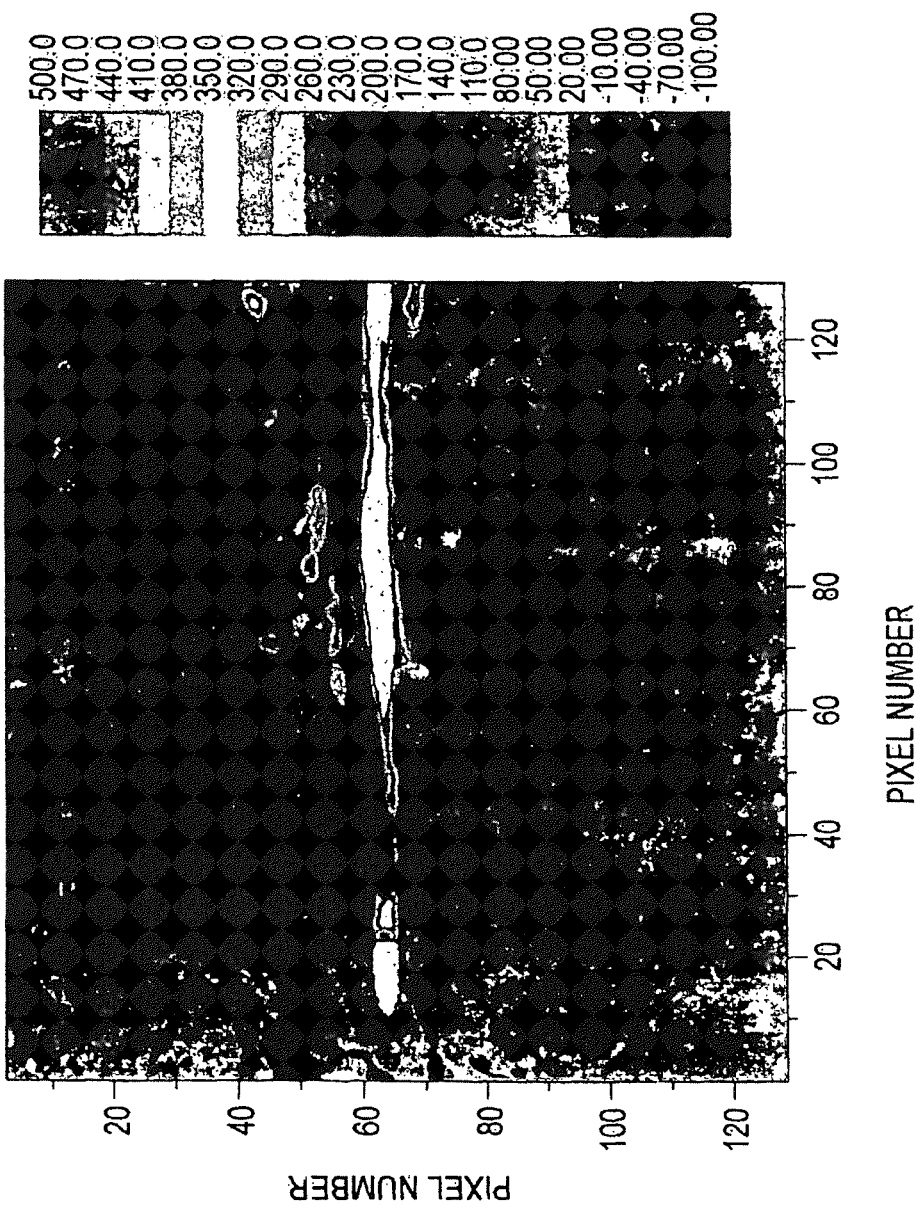
FIG. 19A is a subtracted image after 7 minutes of laser firing on a linear scale for data taken in accordance with a preferred embodiment of this invention (difference image)
Figure 19B:
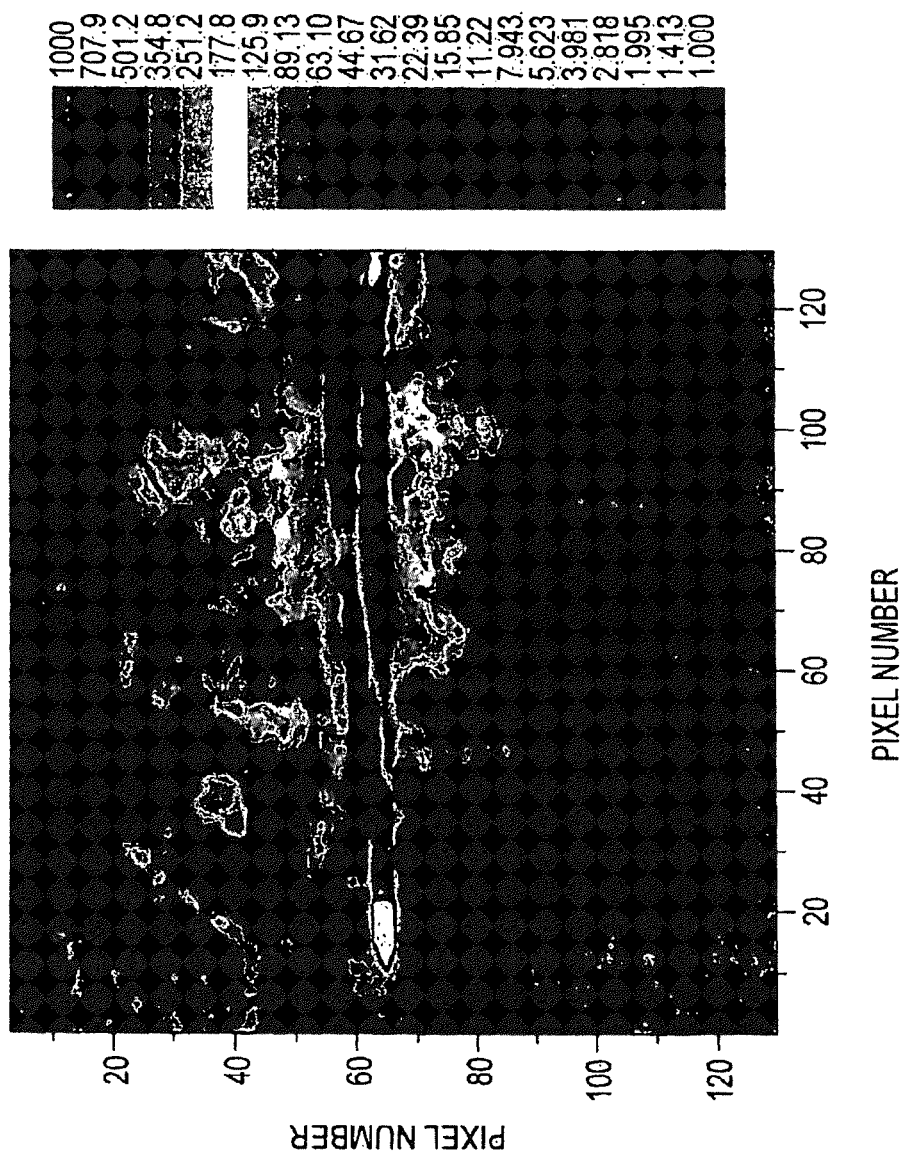
FIG. 19B is a subtracted image after 7 minutes of laser firing on a 5 logarithmic scale for the case corresponding to FIG. 19A (difference image)
Figure 20A:
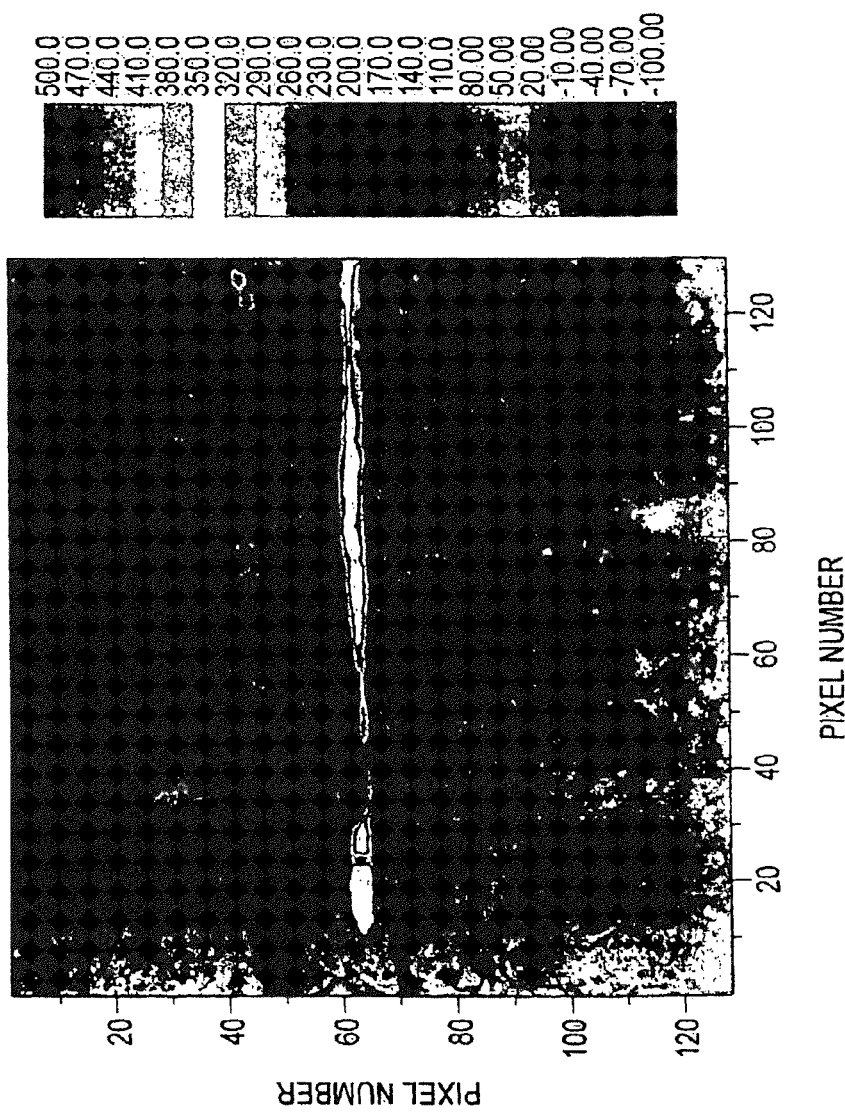
FIG. 20A is a subtracted image after 4 minutes of cooling down on a linear scale for data taken in accordance with a preferred embodiment of this invention (difference image)
Figure 20B:
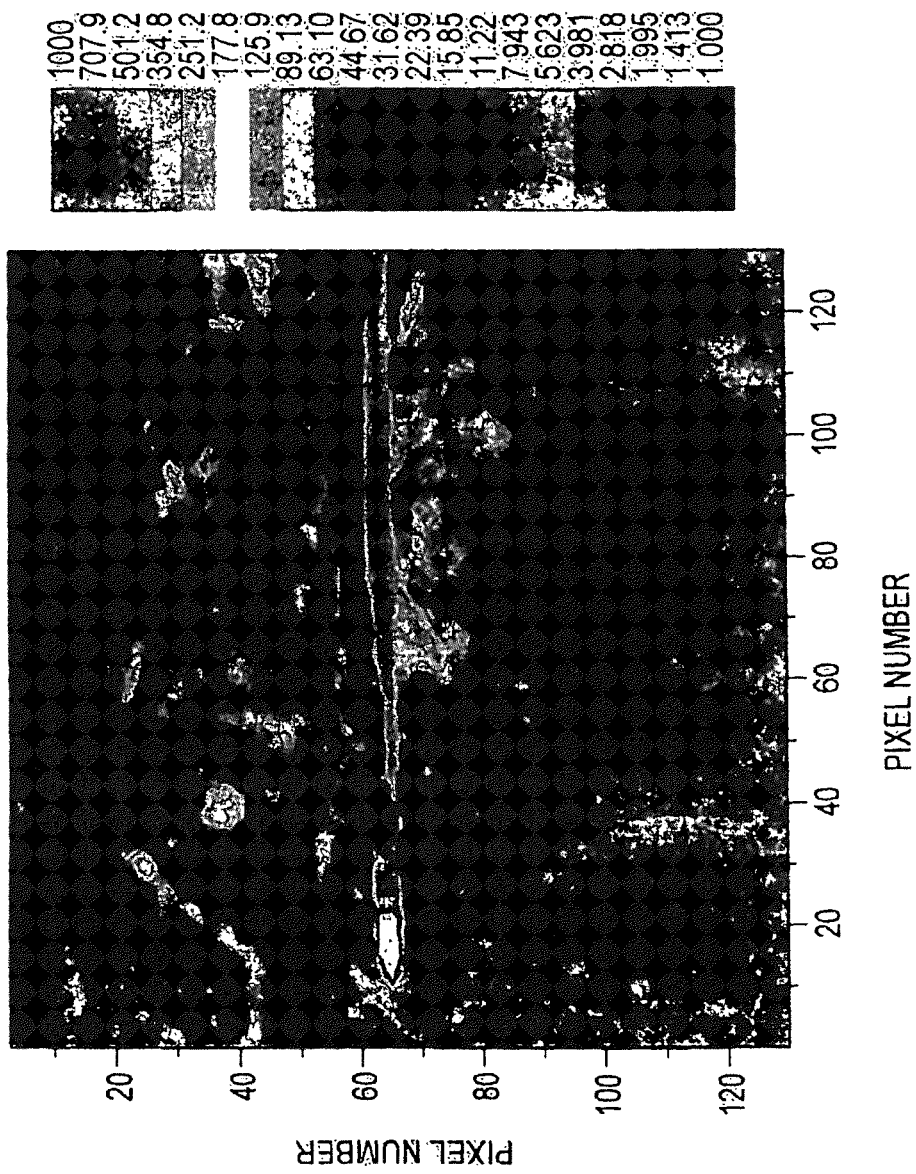
FIG. 20B is a subtracted image on a logarithmic scale for the case corresponding to FIG. 20A (difference image)
Figure 21A:
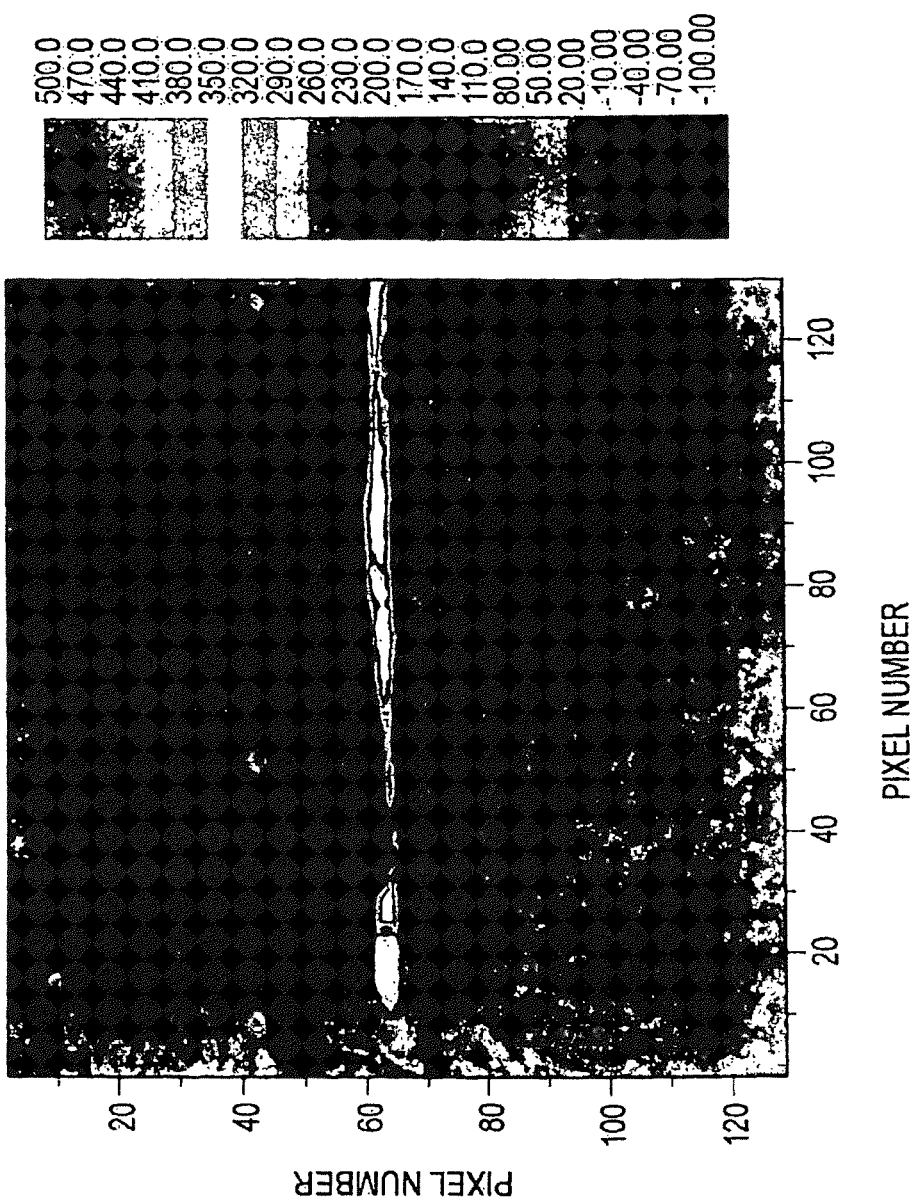
FIG. 21A is a subtracted image after 7 minutes of cooling down on a linear scale for data taken in accordance with a preferred embodiment of this invention (difference image)
Figure 21B:
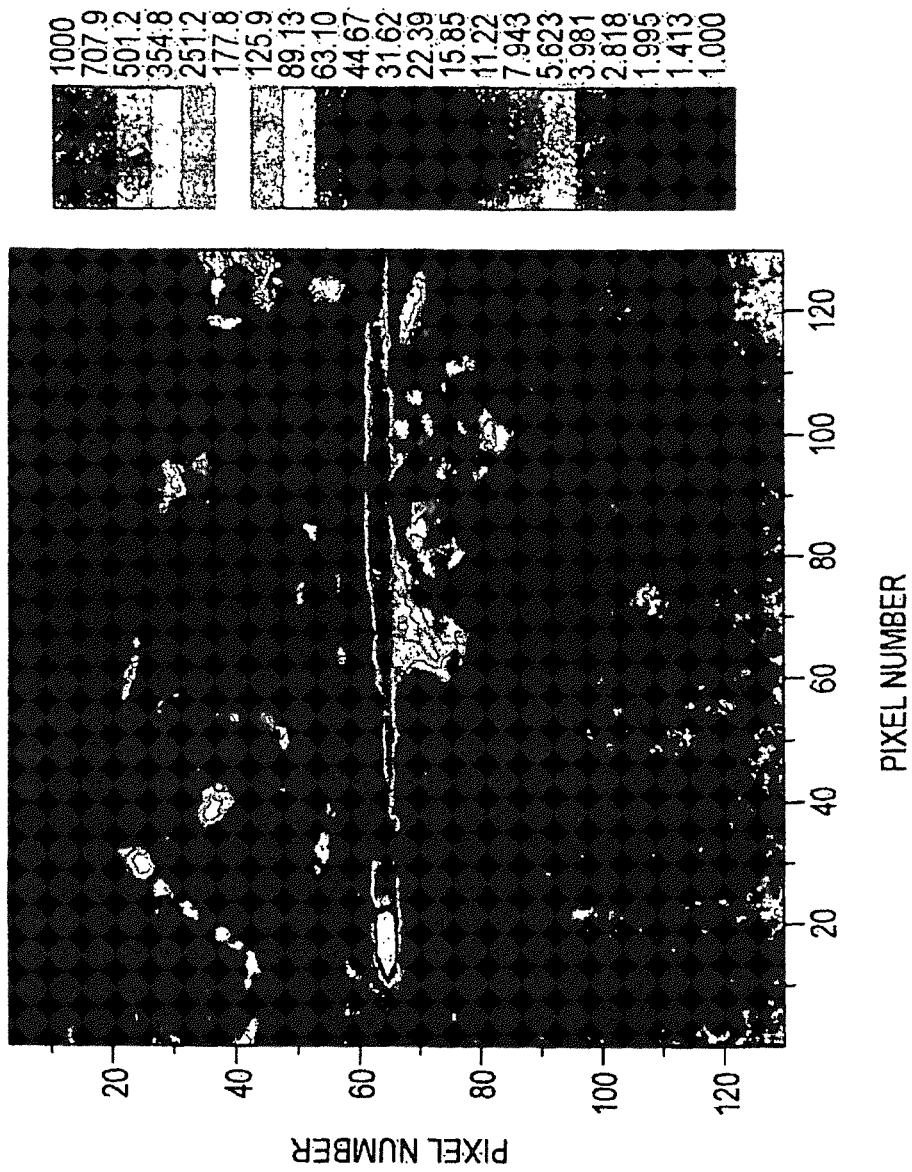
FIG. 21B is a subtracted image on a logarithmic scale corresponding to the case of FIG. 21A (difference image).

Although the images presented here are in a logarithmic scale to 25 highlight the changes around the fiber, the scale will not amplify the temperature range of most interest to hyperthermia when the intensity changes are correlated with temperature (see, FIGS. 16A, 16B and 16C). The temperature range that needs to be monitored most closely in this embodiment of the invention is between 55 and 65° C., which is expected to be in the middle or higher (red) end of the range of intensity changes. Temperatures above 65° C. do not need to be monitored by temperature. In order to amplify the correct temperature range, a more suitable transfer function may be developed to be converted to a color scale (see, FIGS. 16A-21B).

Note:

The minimum pixel intensity is zero and corresponds to total attenuation (i.e., no X-ray photons reaching the camera) and a white image. The maximum pixel intensity is 4095 and corresponds to no attenuation (i.e., all X-ray photons reaching the camera) and a black image. After the images are subtracted, the maximum possible intensity range is from −4095 to 4095. Each pixel corresponds to an area of approximately 50×50 μm in the 1024×1024 pixel images and to approximately 0.4×0.4 mm in the 128×128 pixel images.

Stability Test of Mammo Vision Exposures of Porcine Tissue

This subsection presents an analysis of a stability test of the MAMMOVISION System (85200G-2, Fischer Imaging Co., Denver, Colo.) exposures on fatty porcine tissue during the auto-firing sequence in accordance with this invention.
The Experimental Method:

An approximately 20×8×3 cm piece of fatty porcine tissue with the 25 skin was compressed at room temperature 20° C. with the MAMMOVISION compression paddle. The initial scout was taken in the Autoexposure mode and its parameters were used in the sequential firing. The generator was set manually at 25 kV, 50 mAs, and 100 mA for the following images in the sequential firing. The auto-firing sequence was set to take exposures every 30 seconds for approximately 15 minutes (after the initial scout and stereo images were taken).

The images obtained from this sequence were converted from 1024×1024 pixel images into 128×128 pixel images by averaging 8×8 pixel blocks into one pixel, by using a Turbo C program. These images were then analyzed by another Turbo C program to find pixels that changed in intensity by more than 2%.
Results:

In the 32 128×128 pixel images, only 3 pixels showed variation of greater than 2% (see, Table 7). The maximum variation was 8.8%. All three pixels increased by more than 2% in one image and then returned to approximately the original value in the following image. These results indicate that any image changes of more than 5% in the 128×128 images will be significant (above noise level).

TABLE 7

Coordinates and image number of pixels with over 2% intensity change in the 128 × 128 images

| X-coordinate | Y-coordinate | Image number | Percent change |
| --- | --- | --- | --- |
| 111 | 90 | 6 | 8.79 |
| 111 | 90 | 7 | −8.16 |
| 15 | 70 | 8 | 5.00 |
| 15 | 70 | 9 | −4.95 |
| 107 | 18 | 24 | 4.11 |
| 107 | 18 | 25 | −3.98 |

Conclusion:

This analysis corroborates the earlier findings that the 128×128 pixel images are stable, although those findings indicated that there were no changes above 5% while the results from this analysis indicate that one pixel changed above 5%. This discrepancy may be explained by the relatively low generator mAs value (50 mAs) in this experiment compared to that of the previous experiment (280 mAs), since increasing the mAs value increases contrast. Changes above 5% can be assumed to be due either to thermal expansion or to tissue movement.
Note:

The minimum pixel intensity is zero and corresponds to total attenuation (i.e., no X-ray photons reaching the camera) and a white image. The maximum pixel intensity is 4095 and corresponds to no attenuation (i.e., all X-ray photons reaching the camera) and a black image. Each pixel corresponds to an area of approximately 50×50 μm in the 1024×1024 pixel images and to approximately 0.4×0.4 mm in the 128×128 pixel images.

Although only the presently preferred embodiments have been described in detail above, people with ordinary skill in the art will readily appreciate from the teachings herein that many modifications are possible in the exemplary embodiments without materially departing from the novel teachings and advantages of this invention.

What is claimed is:

1. An apparatus for thermally inducing and monitoring in a patient changes to localized regions of tissue within a volume of tissue of a patient's body during thermotherapy, comprising:
    means for illuminating a volume of tissue of the patient's body with X-rays at a plurality of different times during thermotherapy;
    means for detecting a plurality of portions of said X-rays that have passed through said volume of tissue of the patient's body during said illuminating at a plurality of different times during thermotherapy;
    means for locating at least a portion of the patient's body including said volume of tissue between the means for illuminating and the means for detecting;
    means for generating a plurality of X-ray image signals from said plurality of portions of X-rays detected during said illuminating at a plurality of different times during thermotherapy;
    means for applying localized internal heating to a sub-region of tissue within said volume of tissue, said localized internal heating being sufficient to induce a tissular change within said sub-region of tissue, wherein said means for applying localized internal heating is operable to apply heat to said sub-region of tissue within said volume of tissue from locations external to the patient's body;
    means for generating successive difference image signals during thermotherapy based upon comparisons of X-ray image signals where at least one of the X-ray image signals of each comparison is one of said plurality of X-ray image signals generated during thermotherapy, wherein each of said difference image signals is indicative of temperature changes across said volume of tissue induced by applied localized internal heating corresponding to said compared X-ray image signals, said successive difference image signals comprising information of tissular changes within said volume of tissue induced by the applied localized internal heating; and
    means for successively rendering a plurality of visual images utilizing said plurality of successive difference image signals during thermotherapy, wherein each of said visual images indicates said temperature changes across said volume of tissue.

2. An apparatus according to claim 1, wherein said means for applying localized internal heating is operable to be adjusted to vary the amount of heat applied by said means for applying localized internal heating in response to at least one visual image rendered by said means for successively rendering a plurality of visual images.

3. An apparatus according to claim 1, wherein said means for applying localized internal heating is operable to be repositioned in response to at least one visual image rendered by said means for successively rendering a plurality of visual images.

4. An apparatus according to claim 3, wherein said means for applying localized internal heating is operable to be adjusted to vary the amount of heat applied by said means for applying localized internal heating in response to at least one visual image rendered by said means for successively rendering a plurality of visual images.

5. An apparatus according to claim 1, wherein said means for applying localized internal heating is a means selected from a group comprising microwave sources of radiation, radio-frequency energy sources, and ultrasound energy sources.

6. An apparatus according to claim 1, wherein said means for applying localized internal heating is an ultrasound energy source.

7. An apparatus according to claim 6, wherein said means for generating successive difference image signals is operable to use the same X-ray image signal in each of said comparisons wherein said same X-ray image signal is an X-ray image signal generated prior to any application of localized internal heating.

8. An apparatus according to claim 6, wherein said means for generating successive difference image signals is operable to generate at least one of said difference image signals based upon a comparison of X-ray image signals where both of the X-ray image signals of said comparison are one of said plurality of X-ray image signals generated during thermotherapy.

9. An apparatus according to claim 6, wherein said means for applying localized internal heating is operable to be adjusted to vary the amount of heat applied by said means for applying localized internal heating in response to at least one visual image rendered by said means for successively rendering a plurality of visual images.

10. An apparatus according to claim 6, wherein said means for applying localized internal heating is operable to be repositioned in response to at least one visual image rendered by said means for successively rendering a plurality of visual images.

11. An apparatus according to claim 10, wherein said means for applying localized internal heating is operable to be adjusted to vary the amount of heat applied by said means for applying localized internal heating in response to at least one visual image rendered by said means for successively rendering a plurality of visual images.

12. An apparatus according to claim 10, wherein said means for generating successive difference image signals is operable to generate at least one of said difference image signals based upon a comparison of X-ray image signals where both of the X-ray image signals of said comparison are one of said plurality of X-ray image signals generated during thermotherapy.

13. An apparatus according to claim 10, wherein said means for applying localized internal heating is operable to be adjusted to vary the amount of heat applied by said means for applying localized internal heating in response to at least one visual image rendered by said means for successively rendering a plurality of visual images.

14. An apparatus according to claim 1, wherein said means for applying localized internal heating is operable to apply localized internal heating to said sub-region of tissue while said means for illuminating is illuminating said volume of tissue with X-rays.

15. An apparatus for thermally inducing and monitoring in a patient changes to localized regions of tissue within a volume of tissue of a patient's body during thermotherapy, comprising:
  means for illuminating a volume of tissue of the patient's body with X-rays at a plurality of different times during thermotherapy;
  means for detecting a plurality of portions of said X-rays that have passed through said volume of tissue of the patient's body during said illuminating at a plurality of different times during thermotherapy;
  means for locating at least a portion of the patient's body including said volume of tissue between the means for illuminating and the means for detecting;
  means for generating a plurality of X-ray image signals from said plurality of portions of X-rays detected during said illuminating at a plurality of different times during thermotherapy;
  means for applying localized internal heating to a sub-region of tissue within said volume of tissue, said localized internal heating being sufficient to induce a tissular change within said sub-region of tissue, wherein said means for applying localized internal heating is operable to apply heat to said sub-region of tissue within said volume of tissue from locations external to the patient's body;
  means for generating successive difference image signals during thermotherapy based upon comparisons of X-ray image signals where at least one of the X-ray image signals of each comparison is one of said plurality of X-ray image signals generated during thermotherapy, wherein each of said difference image signals is indicative of temperature changes across said volume of tissue induced by applied localized internal heating corresponding to said compared X-ray image signals, said successive difference image signals comprising information of tissular changes within said volume of tissue induced by the applied localized internal heating; and
  means for successively rendering a plurality of visual images utilizing said plurality of successive difference image signals during thermotherapy, wherein each of said visual images indicates said temperature changes across said volume of tissue, and wherein said means for applying localized internal heating is operable to be adjusted to vary the amount of heat applied by said means for applying localized internal heating in response to at least one visual image rendered by said means for successively rendering a plurality of visual images.

16. An apparatus for thermally inducing and monitoring in a patient changes to localized regions of tissue within a volume of tissue of a patient's body during thermotherapy, comprising:
  means for illuminating a volume of tissue of the patient's body with X-rays at a plurality of different times during thermotherapy;
  means for detecting a plurality of portions of said X-rays that have passed through said volume of tissue of the patient's body during said illuminating at a plurality of different times during thermotherapy;
  means for locating at least a portion of the patient's body including said volume of tissue between the means for illuminating and the means for detecting;
  means for generating a plurality of X-ray image signals from said plurality of portions of X-rays detected during said illuminating at a plurality of different times during thermotherapy;

means for applying localized internal heating to a sub-region of tissue within said volume of tissue, said localized internal heating being sufficient to induce a tissular change within said sub-region of tissue, wherein said means for applying localized internal heating is operable to apply heat to said sub-region of tissue within said volume of tissue from locations external to the patient's body;

means for generating successive difference image signals during thermotherapy based upon comparisons of X-ray image signals where at least one of the X-ray image signals of each comparison is one of said plurality of X-ray image signals generated during thermotherapy, wherein each of said difference image signals is indicative of temperature changes across said volume of tissue induced by applied localized internal heating corresponding to said compared X-ray image signals, said successive difference image signals comprising information of tissular changes within said volume of tissue induced by the applied localized internal heating; and means for successively rendering a plurality of visual images utilizing said plurality of successive difference image signals during thermotherapy, wherein each of said visual images indicates said temperature changes across said volume of tissue, and wherein said means for applying localized internal heating is operable to be repositioned in response to at least one visual image rendered by said means for successively rendering a plurality of visual images.

17. An apparatus according to claim 16, wherein said means for applying localized internal heating is operable to be adjusted to vary the amount of heat applied by said means for applying localized internal heating in response to at least one visual image rendered by said means for successively rendering a plurality of visual images.

* * * * *